United States Patent
Ma et al.

(10) Patent No.: US 12,139,767 B2
(45) Date of Patent: Nov. 12, 2024

(54) COMPOSITION AND METHODS FOR PREDICTING NECROTIZING ENTEROCOLITIS IN PRETERM INFANTS

(71) Applicants: Bing Ma, Clarksville, MD (US); Rose Viscardi, Timonium, MD (US); Jacques Ravel, Laurel, MD (US)

(72) Inventors: Bing Ma, Clarksville, MD (US); Rose Viscardi, Timonium, MD (US); Jacques Ravel, Laurel, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 886 days.

(21) Appl. No.: 17/056,562

(22) PCT Filed: May 22, 2019

(86) PCT No.: PCT/US2019/033488
§ 371 (c)(1),
(2) Date: Nov. 18, 2020

(87) PCT Pub. No.: WO2019/226751
PCT Pub. Date: Nov. 28, 2019

(65) Prior Publication Data
US 2021/0254137 A1    Aug. 19, 2021

Related U.S. Application Data

(60) Provisional application No. 62/674,782, filed on May 22, 2018.

(51) Int. Cl.
*A61K 35/745*        (2015.01)
*C12Q 1/689*         (2018.01)

(52) U.S. Cl.
CPC ....... *C12Q 1/689* (2013.01); *C12Q 2600/106* (2013.01); *C12Q 2600/158* (2013.01)

(58) Field of Classification Search
CPC .......................... G01N 2333/33; A61K 35/745
See application file for complete search history.

(56) References Cited

U.S. PATENT DOCUMENTS

2011/0091445 A1    4/2011   Knol et al.
2015/0182567 A1    7/2015   Lorca
2018/0064739 A1    3/2018   Chichlowski et al.

FOREIGN PATENT DOCUMENTS

CN         107109348 A   *   8/2017   ........... A61K 35/745

OTHER PUBLICATIONS

Stratiki, The effect of a bifidobacter supplemented bovine milk on intestinal permeability of preterm infants. Early human development, (Sep. 2007) vol. 83, No. 9, pp. 575-579 (Year: 2007).*
Taft et al, Intestinal microbiota of preterm infants differ over time and between hospitals. Microbiome, (Oct. 1, 2014) vol. 2, No. 1. am. 36, 1-12. (Year: 2014).*
Underwood, A comparison of two probiotic strains of bifidobacteria in premature infants. The Journal of pediatrics, (Dec. 2013) vol. 163, No. 6, pp. 1585-1591.e9 (Year: 2013).*
International Search Report and Written Opinion of the International Searching Authority, issued Oct. 2, 2019 in corresponding International Patent Application No. PCT/US19/33488.

* cited by examiner

*Primary Examiner* — Qiuwen Mi
(74) *Attorney, Agent, or Firm* — Wenderoth, Lind & Ponack, L.L.P.

(57) ABSTRACT

A correlative finding between increased Clostridiales and/or Bifidobacteriales bacterial abundance in the gut and intestinal barrier maturation of preterm neonates at-risk for development of necrotizing enterocolitis (NEC) is disclosed. These findings form the basis for the methods of identifying preterm infants at risk for developing necrotizing enterocolitis (NEC), the methods of treating such infants, as well as the methods of characterizing intestinal permeability in preterm infants disclosed herein.

26 Claims, 8 Drawing Sheets

(5 of 8 Drawing Sheet(s) Filed in Color)

COMPOSITION AND METHODS FOR PREDICTING NECROTIZING ENTEROCOLITIS IN PRETERM INFANTS

STATEMENT OF FEDERALLY SPONSORED RESEARCH AND DEVELOPMENT

This invention was made with government support under Grant Number AT006945 awarded by the National Institutes of Health. The government has certain rights in the invention.

BACKGROUND OF INVENTION

The colonization of animal intestinal tracts with microorganisms starts at birth and undergoes rapid shifts in composition and structure as the host matures over time (Koenig et al., 2011; Sharon et al., 2013; Grier et al., 2017; de Muinck and Trosvik, 2018). These microorganisms perform essential functions mechanistically linked to the immune system development, nutrient acquisition and energy regulation, opportunistic pathogens suppression, as well as intestinal barrier competency, which includes epithelial metabolism, proliferation and survival, mucin and antimicrobial compound production, and cell-cell communication signaling molecule secretion (Neish, 2009; Belkaid and Hand, 2014; Yu et al., 2016).

Disruption of the intestinal microbiota leads to dysbiosis, a state of ecological imbalance where the community loses diversity, key bacterial species, and more critically metabolic capacity with reduced colonization resistance to opportunistic pathogens (Arrieta et al., 2014). Early life gut dysbiosis is associated with disease susceptibility along with short-term and lifelong health issues, such as necrotizing enterocolitis (Madan et al., 2012), sepsis (Madan et al., 2012), asthma and allergies (Arrieta et al., 2015), type 1 diabetes (Vatanen et al., 2016), celiac disease (Cenit et al., 2015), inflammatory bowel disease (Gevers et al., 2014) and obesity (Cho et al., 2012), among others.

In particular, necrotizing enterocolitis (NEC) is a life-threatening, gastrointestinal emergency that affects approximately 7-10% of preterm neonates with mortality as high as 30-50% (Guner et al., 2009). In this condition, bacteria cross the intestinal wall leading to local and systemic infection and inflammation, and bowel wall necrosis and perforation. Intestinal barrier immaturity, characterized as elevated intestinal permeability, or "leaky gut," is the proximate cause of susceptibility to NEC in preterm neonates (Anand et al., 2007; Fitzgibbons et al., 2009; Fox and Godavitarne, 2012; Bergmann et al., 2013).

It is critical to characterize the preterm infant intestinal microbiota to identify dysbiotic states associated with increased intestinal leakiness, as well as beneficial bacteria associated with improved intestinal barrier function, for subsequent stratification of early diagnosis, early intervention and primary prevention of leaky gut and its sequelae. The present invention is directed to these ends and to other important goals.

BRIEF SUMMARY OF INVENTION

As disclosed herein, the impact of intestinal microbiota development on intestinal mucosal barrier maturation was evaluated in preterm neonates. As discussed in detailed below, a cohort of preterm infants<33 weeks gestation was monitored for intestinal permeability (IP) and fecal microbiota during the first two weeks of life. Rapid decrease in IP indicating intestinal barrier function maturation correlated with significant increase in gut bacteria community diversity. In particular, members of the orders Clostridiales and Bifidobacteriales were highly transcriptionally active, and progressively increasing abundance of Clostridiales was significantly associated with decreased intestinal permeability, an indication of epithelial barrier maturation. Further, neonatal factors previously identified to promote intestinal barrier maturation, including early exclusive breastmilk feeding and shorter duration antibiotic exposure, were found to associate with the early colonization of the intestinal microbiota by members of the Clostridiales, which altogether are associated with improved intestinal barrier function in preterm infants. Given that intestinal barrier immaturity, or "leaky gut," is the proximate cause of susceptibility to necrotizing enterocolitis (NEC) in preterm neonates, these findings form the basis of the invention disclosed herein.

For example, and in a first embodiment, the invention is directed to a method of characterizing intestinal permeability (IP) in a subject.

In a first aspect, this method comprises determining the amount of Clostridiales and/or Bifidobacteriales bacteria in a sample obtained from a subject, wherein when the amount of Clostridiales and/or Bifidobacteriales bacteria is about 5% or less by relative abundance of the total amount of bacteria in the sample, the IP of the subject is characterized as high, and wherein when the amount of Clostridiales and/or Bifidobacteriales bacteria is more than about 5% by relative abundance of the total amount of bacteria in the sample, the IP of the subject is characterized as low. In particular aspects, the subject may be a preterm infant. In particular aspects, the sample is a stool sample.

In a second embodiment, the present invention is directed to a method of treating or preventing high intestinal permeability in a subject.

In a first aspect, this method comprises determining the amount of Clostridiales and/or Bifidobacteriales bacteria in a sample obtained from a subject, and administering a therapeutically effective amount of a treatment or preventive agent for high intestinal permeability to the subject when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering a therapeutically effective amount of a treatment or preventive agent for high intestinal permeability to the subject when the amount of Clostridiales and/or Bifidobacteriales bacteria is within a pre-established range of amounts of Clostridiales and/or Bifidobacteriales bacteria associated with high intestinal permeability. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points and administering a therapeutically effective amount of a treatment or preventive agent for high intestinal permeability to the subject when the amount of Clostridiales and/or Bifidobacteriales bacteria in the samples decreases over time. In particular aspects, the subject may be a preterm infant. In particular aspects, the sample is a stool sample.

In certain aspects, the methods of treating or preventing high intestinal permeability in a subject result in a decrease in IP of at least 10% compared with a subject that does not receive the treatment or preventive agent for high intestinal permeability.

In a third embodiment, the present invention is directed to a method of identifying a subject at elevated risk for developing necrotizing enterocolitis (NEC).

In a first aspect, this method comprises determining the amount of Clostridiales and/or Bifidobacteriales bacteria in a sample obtained from a subject, wherein when the amount of Clostridiales and/or Bifidobacteriales bacteria is about 5% or less by relative abundance of the total amount of bacteria in the sample, the subject is identified as at elevated risk for developing NEC. In particular aspects, the subject may have high intestinal permeability. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and comparing the amount to pre-established ranges of amounts of Clostridiales and/or Bifidobacteriales bacteria associated with NEC, wherein when the amount of Clostridiales and/or Bifidobacteriales bacteria in the sample is within pre-established range of amounts of Clostridiales and/or Bifidobacteriales bacteria associated with NEC, the subject is identified as at elevated risk for developing NEC. In particular aspects, the subject may have high intestinal permeability. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points, wherein when the amount of Clostridiales and/or Bifidobacteriales bacteria in the samples decreases over time, the subject is identified as at elevated risk for developing NEC. In particular aspects, the subject may have high intestinal permeability. In particular aspects, the subject may be a preterm infant. In particular aspects, the sample is a stool sample.

In a fourth embodiment, the present invention is directed to a method of treating or preventing NEC incidence in a subject.

In a first aspect, this method comprises determining the amount of Clostridiales and/or Bifidobacteriales bacteria in a sample obtained from a subject, and administering a therapeutically effective amount of a treatment or preventive agent for NEC to the subject when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering a therapeutically effective amount of a treatment or preventive agent for NEC to the subject when the amount of Clostridiales and/or Bifidobacteriales bacteria is within a pre-established range of amounts of Clostridiales and/or Bifidobacteriales bacteria associated with NEC. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points and administering a therapeutically effective amount of a treatment or preventive agent for NEC to the subject when the amount of Clostridiales and/or Bifidobacteriales bacteria in the samples decreases over time. In particular aspects, the subject may be a preterm infant. In particular aspects, the sample is a stool sample.

In certain aspects, the methods of treating or preventing NEC incidence in a subject result in a decrease in NEC incidence of at least 10% compared with a subject that does not receive the treatment or preventive agent for NEC.

In a fifth embodiment, the present invention is directed to a method of treating or preventing leaky gut in a subject.

In a first aspect, this method comprises determining the amount of Clostridiales and/or Bifidobacteriales bacteria in a sample obtained from a subject, and administering a therapeutically effective amount of a treatment or preventive agent for leaky gut to the subject when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering a therapeutically effective amount of a treatment or preventive agent for leaky gut to the subject when the amount of Clostridiales and/or Bifidobacteriales bacteria is within a pre-established range of amounts of Clostridiales and/or Bifidobacteriales bacteria associated with leaky gut. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points and administering a therapeutically effective amount of a treatment or preventive agent for leaky gut to the subject when the amount of Clostridiales and/or Bifidobacteriales bacteria in the samples decreases over time. In particular aspects, the subject may be a preterm infant. In particular aspects, the sample is a stool sample.

In certain aspects the methods of treating or preventing leaky gut in a subject result in a decrease in IP of at least 10% compared with a subject that does not receive the treatment or preventive agent for leaky gut.

In a sixth embodiment, the present invention is directed to a method of improving intestinal barrier function in a subject.

In a first aspect, this method comprises determining the amount of Clostridiales and/or Bifidobacteriales bacteria in a sample obtained from a subject, and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria is within a pre-established range of amounts of Clostridiales and/or Bifidobacteriales bacteria associated with intestinal barrier malfunction. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria in the samples decreases over time. In particular aspects, the subject may be a preterm infant. In particular aspects, the sample is a stool sample.

In certain aspects, the methods of improving intestinal barrier function in a subject result in an improvement in function of at least 10% compared with a subject that does not receive the LBP.

In a seventh embodiment, the present invention is directed to a method of promoting intestinal barrier maturation in a subject.

In a first aspect, this method comprises determining the amount of Clostridiales and/or Bifidobacteriales bacteria in a sample obtained from a subject, and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria is within a pre-established range of amounts of Clostridiales and/or Bifidobacteriales bacteria associated with an immature intestinal barrier. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria in the samples decreases over time. In particular aspects, the subject may be a preterm infant. In particular aspects, the sample is a stool sample.

In certain aspects, the methods of promoting intestinal barrier maturation in a subject result in a maturation of at least 10% compared with a subject that does not receive the LBP.

In an eighth embodiment, the present invention is directed to a method of reducing gut inflammation in a subject.

In a first aspect, this method comprises determining the amount of Clostridiales and/or Bifidobacteriales bacteria in a sample obtained from a subject, and administering to the subject a therapeutically effective amount of an agent to reduce gut inflammation when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering to the subject a therapeutically effective amount of an agent to reduce gut inflammation when the amount of Clostridiales and/or Bifidobacteriales bacteria is within a pre-established range of amounts of Clostridiales and/or Bifidobacteriales bacteria associated with high gut inflammation. In particular aspects, the subject may be a preterm infant. In particular aspects, the sample is a stool sample.

In certain aspects, the methods of reducing gut inflammation in a subject result in a decrease in inflammation of at least 10% compared with a subject that does not receive the agent to decrease gut inflammation.

In a ninth embodiment, the present invention is directed to a method of maintaining gut homeostasis in a subject.

In a first aspect, this method comprises determining the amount of Clostridiales and/or Bifidobacteriales bacteria in a sample obtained from a subject, and administering to the subject a therapeutically effective amount of an agent to induce gut homeostasis when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering to the subject a therapeutically effective amount of an agent to induce gut homeostasis when the amount of Clostridiales and/or Bifidobacteriales bacteria is within a pre-established range of amounts of Clostridiales and/or Bifidobacteriales bacteria associated with dysregulated gut homeostasis. In particular aspects, the subject may be a preterm infant. In particular aspects, the sample is a stool sample.

In certain aspects, the methods of maintaining gut homeostasis in a subject result in an improvement in gut homeostasis of at least 10% compared with a subject that does not receive the agent to induce gut homeostasis.

In a tenth embodiment, the present invention is directed to a live biotherapeutic product (LBP) comprising a culture of one or more of Clostridiales, *Lactobacillus*, Bifidobacteriales and Negativicutes bacteria.

In each of the embodiments and aspects of the invention defined herein, the preterm infant is an infant of less than 37 weeks of gestational age.

In relevant embodiments and aspects of the invention defined herein, the amount of Clostridiales and/or Bifidobacteriales bacteria in the sample may be based, for example, on the relative abundance of one or more selected genes corresponding to the bacteria in the sample or the relative abundance amount of the bacteria in the sample. When the amount of bacteria in the sample is based on the relative abundance of one or more selected genes, the genes may be, for example, a 16S rRNA gene variable region of the bacteria, such as, but not limited to, the V3-V4 variable region of 16S rRNA genes.

In relevant embodiments and aspects of the invention defined herein, when samples are obtained from a subject at two or more time points, the time points are separated by at least 7 days plus or minus 1 to 2 days.

In relevant embodiments and aspects of the invention defined herein, the LBP comprises Clostridiales and Bifidobacteriales. In other embodiments and aspects of the invention, the LBP comprises each of Clostridiales, *Lactobacillus* and Bifidobacteriales. In further embodiments and aspects of the invention, the LBP comprises each of Clostridiales, *Lactobacillus*, Bifidobacteriales and Negativicutes. In further embodiments and aspects of the invention, the LBP comprises one or more of *Bifidobacterium, Lactobacillus*, Acetoanaerobium, Acidaminobacter, Anaerocellum, Anaerovirgula, Anaerovorax, Carboxydocella, Casaltella, Epulopiscium, Fenollaria, Flavonifractor, Fusibacter, Gottschalkia, Guggenheimella, Howardella, Intestinimonas, Levyella, Metabacterium, Mogibacterium, Natranaerovirga, Proteiniborus, Proteocatella, Pseudoflavonifractor, Sulfobacillus, Thermaerobacter, and *Veillonella* bacteria.

In relevant embodiments and aspects of the invention defined herein, a decrease in the amount of Clostridiales and/or Bifidobacteriales bacteria in the samples over time is a decrease of at least about 10%.

In some of the embodiments and aspects of the invention, the methods include administering a treatment to the subject, such as a treatment for (i) high intestinal permeability, (ii) NEC, and (iii) leaky gut. Suitable treatment includes, but are not limited to, LBP, antibiotics, prebiotics, synbiotics, and intestinal environment parameters modifying small molecules.

In some of the embodiments and aspects of the invention, the methods include administering a preventive agent to the subject, such as an agent for preventing (i) high intestinal permeability, (ii) NEC, and (iii) leaky gut. Suitable agents include, but are not limited to, LBP, antibiotics, prebiotics, synbiotics, and intestinal environment parameters modifying small molecules.

In some of the embodiments and aspects of the invention, the methods include administering an agent to modulate gut inflammation or induce gut homeostasis to the subject. Suitable agents include, but are not limited to, LBP, antibiotics, prebiotics, synbiotics, and intestinal environment parameters modifying small molecules.

The methods of the invention that include treatment or prevention may further comprise administering breast milk to the subject, especially when the subject is a preterm infant, and/or reducing exposure of the subject to antibiotics. As discussed in the examples, these additional steps have been shown to increase Clostridiales and/or Bifidobacteriales bacteria abundance in the subject. Such an increase may lead to improved treatment outcomes and further reduce the likelihood that the subject will develop one of the conditions or diseases discussed herein.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits of the invention.

BRIEF DESCRIPTION OF DRAWINGS

The application file contains at least one drawing executed in color. Copies of this patent application publication with color drawing(s) will be provided by the Office upon request and payment of the necessary fee.

DETAILED DESCRIPTION OF THE INVENTION

1. Definitions

Figure 1:
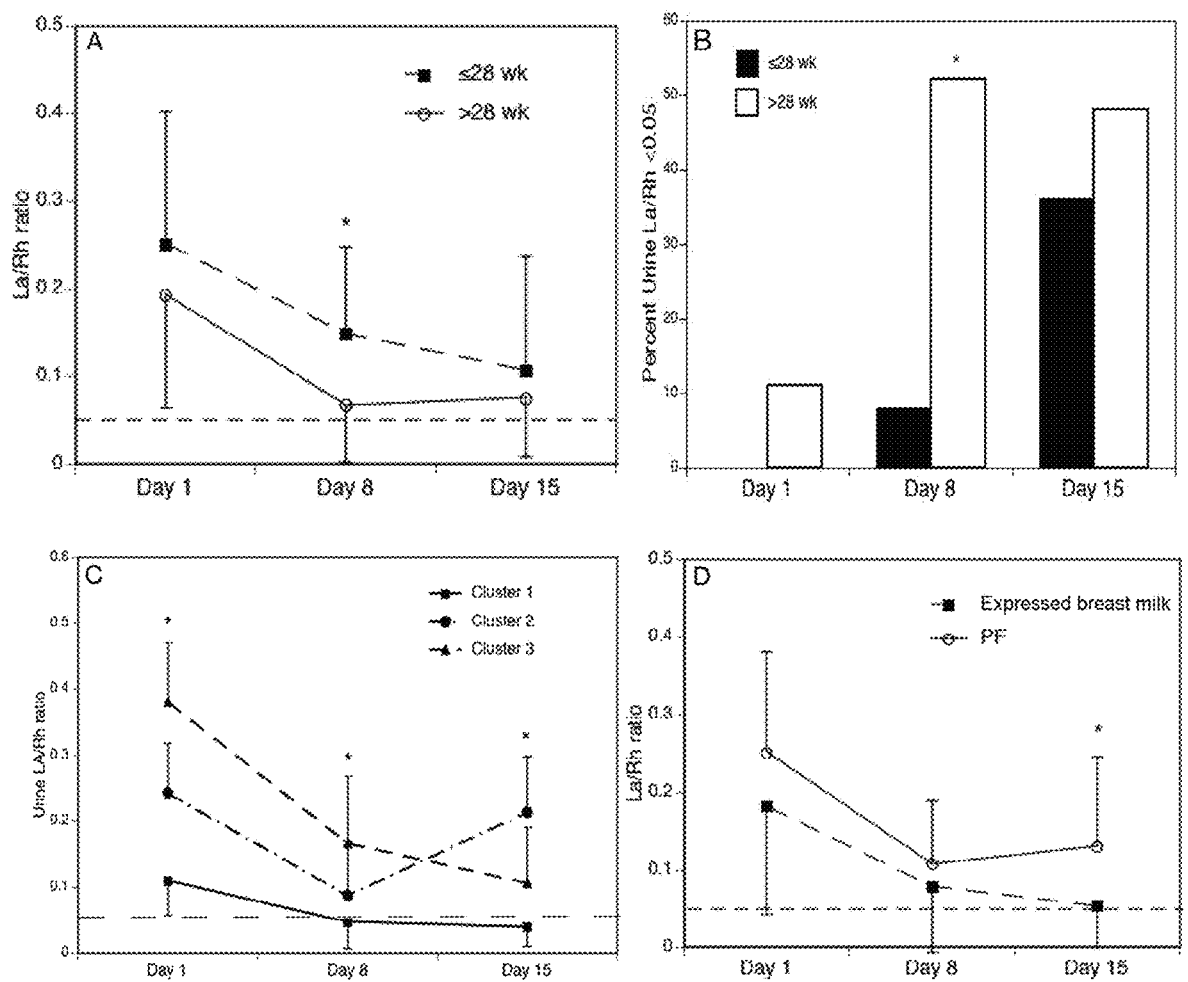
FIG. 1. A, Urinary La/Rh ratio by GA strata and study time points. B, percent with normal intestinal barrier function (La/Rh ratio<0.05). C and D, cluster IP patterns and exclusive breast milk feeding. Data are expressed as mean±SD or present. * P<. 05.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

Despite the critical role of the microbial community in intestinal barrier function, its contributions to newborn intestinal permeability (IP) has been unknown. In particular, the microbiota of preterm neonates with measured elevated IP, a high-risk population for NEC, has not been previously studied. However, the inventors hypothesized that the intestinal microbiota plays a pivotal role in modulating IP and that the presence of "beneficial" bacteria will be associated with improved intestinal barrier function in preterm infants.

As reported in detail below, to investigate this hypothesis three time points during the first 2 weeks of life were sampled in preterm human infants, which is a critical period corresponding to the initiation of the intestinal microbiota development process (Mackie et al., 1999; Mshvildadze et al., 2008; Saleem et al., 2017). A rapid decrease in IP was found to correlate with an increasing abundance of Clostridiales, indicating intestinal barrier function maturation over the first 2 weeks of life with a shift in the composition and structure in intestinal microbial community. Further, neonatal factors previously identified to promote intestinal barrier maturation, including early exclusive breastmilk feeding and less antibiotic exposure, were found to associate with the early colonization of the intestinal microbiota by members of the Clostridiales, which altogether are associated with improved intestinal barrier function in preterm infants. The results highlight the multifactorial processes involved in intestinal barrier maturation, and the importance of considering microbiological and neonatal factors when diagnosing, monitoring, and modulating IP in preterm infants in NEC treatment and prevention. The invention disclosed herein is based on these findings.

As will be apparent from the various embodiments and aspects of the invention described and defined herein, the basis for the invention is the discovery of a correlation between the amount of bacteria from the orders Clostridiales or Bifidobacteriales in the gut of a subject and intestinal permeability. Generally, and particularly in the case of preterm infants, when the amount of Clostridiales and/or Bifidobacteriales bacteria is about 5% or less by relative abundance of the total amount of bacteria in a sample from a subject, the intestinal permeability (IP) of the subject is characterized as high, and wherein when the amount of Clostridiales and/or Bifidobacteriales bacteria is more than about 5% by relative abundance of the total amount of bacteria in the sample, the IP of the subject is characterized as low. Higher IP is generally preferred over low IP. Based on this surprising correlation, the various related embodiments of the invention were developed.

Methods of Characterizing Intestinal Permeability (IP)

For example, the invention is directed to a method of characterizing intestinal permeability (IP) in a subject. Characterization of IP in a subject means primarily determining whether the IP of the subject is low or high, relative to a subject having a normal level of IP. In most cases, low IP is equivalent to normal IP and means the permeability of the subject's intestine functions normally.

This method generally comprises determining the amount of Clostridiales and/or Bifidobacteriales bacteria in a sample obtained from a subject, wherein when the amount of Clostridiales and/or Bifidobacteriales bacteria is about 5% or less by relative abundance of the total amount of bacteria in the sample, the IP of the subject is characterized as high, and wherein when the amount of Clostridiales and/or Bifidobacteriales bacteria is more than about 5% by relative abundance of the total amount of bacteria in the sample, the IP of the subject is characterized as low. In particular aspects, the subject may be a preterm infant. In particular aspects, the sample is a stool sample.

Methods of Treating or Preventing High Intestinal Permeability

The invention is also directed to a method of treating or preventing high intestinal permeability (IP) in a subject. High IP means that the IP of the subject is high, relative to a subject having a normal level of IP. High IP also means the permeability of the subject's intestine is not functioning normally in that barrier function of the intestine improperly permits substances to enter the bloodstream that would normally be retained in the gut.

In a first aspect, this method comprises determining the amount of Clostridiales and/or Bifidobacteriales bacteria in a sample obtained from a subject, and administering a therapeutically effective amount of a treatment or preventive agent for high intestinal permeability to the subject when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering a therapeutically effective amount of a treatment or preventive agent for high intestinal permeability to the subject when the amount of Clostridiales and/or Bifidobacteriales bacteria is within a pre-established range of amounts of Clostridiales and/or Bifidobacteriales bacteria associated with high intestinal permeability. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points and administering a therapeutically effective amount of a treatment or preventive agent for high intestinal permeability to the subject when the amount of Clostridiales and/or Bifidobacteriales bacteria in the samples decreases over time. In particular aspects, the subject may be a preterm infant. In particular aspects, the sample is a stool sample.

These methods thus include treating or preventing high intestinal permeability in a subject, such as a preterm infant. In such methods, a decrease in IP of at least about 5, 10, 15, 20, 25, 30, 35, 40, 45, 50, 55, 60, 65, 70, 75, 80, 85, 90, 95% or more, compared with a subject that does not receive the treatment or preventive agent for high intestinal permeability, is achieved. In one aspect, a decrease in IP of at least about 10% is achieved.

Methods of Identifying Elevated Risk for NEC

The invention is further directed to a method of identifying a subject at elevated risk for developing necrotizing enterocolitis (NEC). NEC is a life-threatening, gastrointestinal emergency that affects approximately 7-10% of preterm neonates with mortality as high as 30-50% (Guner et al., 2009). In this condition, bacteria cross the intestinal wall leading to local and systemic infection and inflammation, and bowel wall necrosis and perforation. Intestinal barrier immaturity, characterized as elevated intestinal permeability, or "leaky gut," is the proximate cause of susceptibility to NEC in preterm neonates (Anand et al., 2007; Fitzgibbons et al., 2009; Fox and Godavitarne, 2012; Bergmann et al., 2013).

In a first aspect, this method comprises determining the amount of Clostridiales and/or Bifidobacteriales bacteria in a sample obtained from a subject, wherein when the amount of Clostridiales and/or Bifidobacteriales bacteria is about 5% or less by relative abundance of the total amount of bacteria in the sample, the subject is identified as at elevated risk for developing NEC. In particular aspects, the subject may have high intestinal permeability. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and comparing the amount to pre-established ranges of amounts of Clostridiales and/or Bifidobacteriales bacteria associated with NEC, wherein when the amount of Clostridiales and/or Bifidobacteriales bacteria in the sample is within the pre-established range of amounts of Clostridiales and/or Bifidobacteriales bacteria associated with NEC, the subject is identified as at elevated risk for developing NEC. In particular aspects, the subject may have high intestinal permeability. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points, wherein when the amount of Clostridiales and/or Bifidobacteriales bacteria in the samples decreases over time, the subject is identified as at elevated risk for developing NEC. In particular aspects, the subject may have high intestinal permeability. In particular aspects, the subject may be a preterm infant. In particular aspects, the sample is a stool sample.

As used herein, the phrase "at elevated risk for developing necrotizing enterocolitis" means the subject, such as a preterm infant, has a risk of developing necrotizing enterocolitis that is higher than a subject in which the amount of Clostridiales and/or Bifidobacteriales bacteria in a sample from the subject is more than about 5% by relative abundance of the total amount of bacteria in the sample.

Methods of Treating or Preventing NEC

The invention is also directed to a method of treating or preventing NEC incidence in a subject.

In a first aspect, this method comprises determining the amount of Clostridiales and/or Bifidobacteriales bacteria in a sample obtained from a subject, and administering a therapeutically effective amount of a treatment or preventive agent for NEC to the subject when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering a therapeutically effective amount of a treatment or preventive agent for NEC to the subject when the amount of Clostridiales and/or Bifidobacteriales bacteria is within a pre-established range of amounts of Clostridiales and/or Bifidobacteriales bacteria associated with NEC. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points and administering a therapeutically effective amount of a treatment or preventive agent for NEC to the subject when the amount of Clostridiales and/or Bifidobacteriales bacteria in the samples decreases over time. In particular aspects, the subject may be a preterm infant. In particular aspects, the sample is a stool sample.

These methods thus include treating or preventing NEC incidence in a subject, such as a preterm infant. In such methods, a decrease in NEC incidence of at least about 5, 10, 15, 20, 25, 30, 35, 40, 45, 50, 55, 60, 65, 70, 75, 80, 85, 90, 95% or more, compared with a subject that does not receive the treatment or preventive agent for NEC, is achieved. In one aspect, a decrease in NEC incidence of at least about 10% is achieved.

Method of Treating or Preventing Leaky Gut

The invention is further directed to a method of treating or preventing leaky gut in a subject. As used herein, the phrase "leaky gut" means the condition where the tight junctions between the cells of the intestinal walls malfunction and allow substances, such as bacteria and toxins that are normally retained in the gut, to pass from the gut into the bloodstream. When the gut is "leaky", bacteria and toxins are disseminated via the blood stream which in turn can lead to widespread inflammation and possibly trigger a reaction from the immune system. Symptoms associated with leaky gut syndrome include bloating, food sensitivities, fatigue, digestive issues and skin problems.

In a first aspect, this method comprises determining the amount of Clostridiales and/or Bifidobacteriales bacteria in a sample obtained from a subject, and administering a therapeutically effective amount of a treatment or preventive agent for leaky gut to the subject when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering a therapeutically effective amount of a treatment or preventive agent for leaky gut to the subject when the amount of Clostridiales and/or Bifidobacteriales bacteria is within a pre-established range of amounts of Clostridiales and/or Bifidobacteriales bacteria associated with leaky gut. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points and administering a therapeutically effective amount of a treatment or preventive agent for leaky gut to the subject when the amount of Clostridiales and/or Bifidobacteriales bacteria in the samples decreases over time. In particular aspects, the subject may be a preterm infant. In particular aspects, the sample is a stool sample.

These methods thus include treating or preventing leaky gut in a subject, such as a preterm infant. In such methods, a decrease in IP of at least about 5, 10, 15, 20, 25, 30, 35, 40, 45, 50, 55, 60, 65, 70, 75, 80, 85, 90, 95% or more, compared with a subject that does not receive the treatment or preventive agent for leaky gut, is achieved. In one aspect, a decrease in IP of at least about 10% is achieved.

Methods of Improving Intestinal Barrier Function

The present invention is also directed to a method of improving intestinal barrier function in a subject. An improvement in intestinal barrier function is an improvement in one or more of the barrier functions typically associated with the intestine, including, but not limited to, blocking entry of bacteria and toxins from passing through the wall of the intestine and entering the bloodstream.

In a first aspect, this method comprises determining the amount of Clostridiales and/or Bifidobacteriales bacteria in a sample obtained from a subject, and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria is within a pre-established range of amounts of Clostridiales and/or Bifidobacteriales bacteria associated with intestinal barrier malfunction. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria in the samples decreases over time. In particular aspects, the subject may be a preterm infant. In particular aspects, the sample is a stool sample.

The methods thus include improving intestinal barrier function in a subject, such as a preterm infant. In such methods, an improvement in intestinal barrier function of at least about 5, 10, 15, 20, 25, 30, 35, 40, 45, 50, 55, 60, 65, 70, 75, 80, 85, 90, 95% or more, compared with a subject that does not receive LBP, is achieved. In one aspect, an improvement in intestinal barrier function of at least about 10% is achieved.

Methods of Promoting Intestinal Barrier Maturation

The invention is further directed to a method of promoting intestinal barrier maturation in a subject. Promoting intestinal barrier maturation means increasing the ability of the intestine to act as a barrier. Barrier functions typically associated with the intestine include, but are not limited to, blocking entry of bacteria and toxins into the bloodstream via passage through the wall of the intestine.

In a first aspect, this method comprises determining the amount of Clostridiales and/or Bifidobacteriales bacteria in a sample obtained from a subject, and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria is within a pre-established range of amounts of Clostridiales and/or Bifidobacteriales bacteria associated with an immature intestinal barrier. In particular aspects, the subject may be a preterm infant. In particular aspects, the sample is a stool sample.

In a third aspect, this method comprises determining the amount of Clostridiales and/or Bifidobacteriales bacteria in samples obtained from a subject at two or more time points and administering a therapeutically effective amount of a live biotherapeutic product (LBP) comprising a culture of one or more of Clostridiales, *Lactobacillus*, Bifidobacteriales and Negativicutes bacteria to the subject when the amount of Clostridiales and/or Bifidobacteriales bacteria in the samples decreases over time. In particular aspects, the subject may be a preterm infant. In particular aspects, the sample is a stool sample.

These methods thus include promoting intestinal barrier maturation in a subject, such as a preterm infant. In such methods, an a maturation of the intestinal barrier of at least about 5, 10, 15, 20, 25, 30, 35, 40, 45, 50, 55, 60, 65, 70, 75, 80, 85, 90, 95% or more, compared with a subject that does not receive LBP, is achieved. In one aspect, a maturation of the intestinal barrier of at least about 10% is achieved.

Methods of Reducing Gut Inflammation

The invention is also directed to a method of reducing gut inflammation in a subject. Such methods serve to reduce the level of inflammation in the gut to normal or near-normal levels.

In a first aspect, this method comprises determining the amount of Clostridiales and/or Bifidobacteriales bacteria in a sample obtained from a subject, and administering to the subject a therapeutically effective amount of an agent to reduce gut inflammation when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering to the subject a therapeutically effective amount of an agent to reduce gut inflammation when the amount of Clostridiales and/or Bifidobacteriales bacteria is within a pre-established range of amounts of Clostridiales and/or Bifidobacteriales bacteria associated with high gut inflammation. In particular aspects, the subject may be a preterm infant. In particular aspects, the sample is a stool sample.

These methods thus include reducing gut inflammation in a subject, such as a preterm infant. In such methods, a decrease in gut inflammation of at least about 5, 10, 15, 20, 25, 30, 35, 40, 45, 50, 55, 60, 65, 70, 75, 80, 85, 90, 95% or more, compared with a subject that does not receive an agent to modulate gut inflammation, is achieved. In one aspect, a decrease in gut inflammation of at least about 10% is achieved.

Methods of Maintaining Gut Homeostasis

The invention is further directed to a method of maintaining gut homeostasis in a subject. Such methods take a prophylactic approach the ensuring normal gut function in the subject. Such methods generally ensure a normal and healthy gut microbiota is maintained in the subject.

In a first aspect, this method comprises determining the amount of Clostridiales and/or Bifidobacteriales bacteria in a sample obtained from a subject, and administering to the subject a therapeutically effective amount of an agent to induce gut homeostasis when the amount of Clostridiales and/or Bifidobacteriales bacteria in the sample is about 5% or less by relative abundance of the total amount of bacteria. In particular aspects, the subject may be a preterm infant. In particular aspects, the sample is a stool sample.

In a second aspect, this method comprises determining the amount of Clostridiales and/or Bifidobacteriales bacteria in a sample obtained from a subject, and administering to the subject a therapeutically effective amount of an agent to induce gut homeostasis when the amount of Clostridiales and/or Bifidobacteriales bacteria is within a pre-established range of amounts of Clostridiales and/or Bifidobacteriales bacteria associated with dysregulated gut homeostasis. In particular aspects, the subject may be a preterm infant. In particular aspects, the sample is a stool sample.

These methods thus include maintaining gut homeostasis in a subject, such as a preterm infant. In such methods, an improvement in gut homeostasis of at least about 5, 10, 15, 20, 25, 30, 35, 40, 45, 50, 55, 60, 65, 70, 75, 80, 85, 90, 95% or more, compared with a subject that does not receive an agent to induce gut homeostasis, is achieved. In one aspect, an improvement in gut homeostasis of at least about 10% is achieved.

Live Biotherapeutic Products

The invention is also directed to a live biotherapeutic product (LBP) comprising a culture of one or more of Clostridiales, *Lactobacillus*, Bifidobacteriales and/or Negativicutes bacteria. The invention is thus directed to LBPs comprising Clostridiales and Bifidobacteriales bacteria, or Clostridiales and *Lactobacillus* bacteria, Clostridiales and Negativicutes bacteria, or Bifidobacteriales and *Lactobacillus* bacteria, or Bifidobacteriales and Negativicutes bacteria, or *Lactobacillus* and Negativicutes bacteria, or each of Clostridiales, Bifidobacteriales and *Lactobacillus* bacteria, or each of Clostridiales, Bifidobacteriales and Negativicutes bacteria or each of Bifidobacteriales, *Lactobacillus* and Negativicutes bacteria, or each of Clostridiales, *Lactobacillus*, Bifidobacteriales and Negativicutes bacteria. Particular genera of bacteria from these groups that may be included in LBPs of the invention include those known in the art to be effective in such formulations including, but are not limited to, one or more of *Bifidobacterium, Lactobacillus*, Acetoanaerobium, Acidaminobacter, Anaerocellum, Anaerovirgula, Anaerovorax, Carboxydocella, Casaltella, Epulopiscium, Fenollaria, Flavonifractor, Fusibacter, Gottschalkia, Guggenheimella, Howardella, Intestinimonas, Levyella, Metabacterium, Mogibacterium, Natranaerovirga, Proteiniborus, Proteocatella, Pseudoflavonifractor, Sulfobacillus, Thermaerobacter, and *Veillonella* bacteria.

Subjects

In each of the embodiments and aspects of the invention defined herein, the subject is a human, a non-human primate, bird, horse, cow, goat, sheep, a companion animal, such as a dog, cat or rodent, or other mammal. In particular embodiments and aspects, the subject is a human, such as a preterm infant, a term infant, a toddler, a child, a pre-teen, a teenager, or an adult. A preterm infant is an infant of less than 33, 34, 35, 36 or 37 weeks of gestational age.

Samples

In each of the embodiments and aspects of the invention defined herein, the sample contains gut bacteria. In preferred aspects, the sample is a stool sample. However, it will be apparent that other biological specimens obtained from a subject will also contain sufficient quantities of gut bacteria for use in the methods of the invention. Such specimens include, but are not limited to, rectal swabs, intestinal biopsy, intraluminal stool and fluid, stomach contents such as those obtained via gastric lavage, and colon contents such as those obtained via an enema.

Bacteria Amounts

In relevant embodiments and aspects of the invention defined herein, the amount of Clostridiales and/or Bifidobacteriales bacteria in a sample is the amount based on the total amount of bacteria present in a sample. The amount of selected bacteria in a sample may be determined using well-known techniques. For example, the amount may be based on the relative abundance of one or more genes corresponding to selected bacteria in the sample or the relative amount of the bacteria in the sample by weight. When the amount of bacteria in the sample is based on the relative abundance of one or more genes, the genes may be, for example, a 16S rRNA gene variable region of the bacteria, such as, but not limited to, the V3-V4 variable region of 16S rRNA genes.

In some of the embodiments and aspects of the invention, samples obtained at different time points are analyzed. When samples are obtained from a subject at two or more time points, the time points are separated by at least 1, 2, 3, 4, 5, 6, 7, 8, 9 or 10 days. In a preferred example, the time points are separated by 7 days plus or minus 1 to 2 days. In certain embodiments and aspects of the invention, samples may be obtained from a subject at 3, 4, 5, 6 or more time points.

In some of the embodiments and aspects of the invention, the methods include observing a decrease in the amount of Clostridiales and/or Bifidobacteriales bacteria in the samples over time. The decrease is decrease of at least about 5, 10, 15, 20, 25, 30, 35, 40, 45, 50, 55, 60, 65, 70, 75, 80, 85, 90, 95% or more of the relative abundance of bacteria in the samples over time. In one aspect, the decrease is at least about 10% of the relative abundance of bacteria in the samples over time.

In some of the embodiments and aspects of the invention, the methods include administering a treatment to the subject, such as a treatment for (i) high intestinal permeability, (ii) NEC, (iii) leaky gut, (iv) reducing gut inflammation, and (v) inducing gut homeostasis. Suitable treatments include, but are not limited to, LBP, antibiotics, prebiotics, synbiotics, and intestinal environment parameters modifying small molecules.

In some of the embodiments and aspects of the invention, the methods include administering a preventive agent to the subject, such as an agent for preventing (i) high intestinal permeability, (ii) NEC, and (iii) leaky gut. Suitable agents include, but are not limited to, LBP, antibiotics, prebiotics, synbiotics, and intestinal environment parameters modifying small molecules.

In some of the embodiments and aspects of the invention, the methods include administering an agent to modulate gut inflammation or induce gut homeostasis to the subject. Suitable agents include, but are not limited to, LBP, antibiotics, prebiotics, synbiotics, and intestinal environment parameters modifying small molecules.

The methods of the invention that include treatment or prevention may further comprise administering breast milk to the subject, especially when the subject is a preterm infant, and/or reducing exposure of the subject to antibiotics. As discussed in the examples, these additional steps have been shown to increase Clostridiales and/or Bifidobacteriales bacteria abundance in the subject. Such an increase may lead to improved treatment outcomes and further reduce the likelihood that the subject will develop one of the conditions or diseases discussed herein.

As used herein, the phrase "pre-established range of amounts of Clostridiales and/or Bifidobacteriales bacteria" means amounts of Clostridiales and/or Bifidobacteriales bacteria determined in earlier experiments to be associated with certain conditions or diseases, such as high intestinal permeability, necrotizing enterocolitis, leaky gut, intestinal barrier malfunction, immature intestinal barrier, high gut inflammation, and dysregulated gut homeostasis.

As used herein, the phrase "high intestinal permeability", "the IP of the subject is characterized as high" and related expressions means the subject exhibits a La/Rh ratio of >0.05. Conversely, the phrase "low intestinal permeability", "the IP of the subject is characterized as low" and related expressions means the subject exhibits a La/Rh ratio of ≤0.05. This high or low IP definition was validated and applied previously (Saleem et al., 2017). The lactulose/rhamnose ratio (La/Rh ratio) is calculated as the fractional excretion of lactulose divided by that of rhamnose (Rouwet et al., 2002; Haase et al., 2000; Mishra et al., 2012; Beach et al., 1982).

As used herein, the terms "treat", "treating", and "treatment" have their ordinary and customary meanings, and include one or more of: blocking, ameliorating, or decreasing in severity and/or frequency a symptom of a disease or condition defined or otherwise mentioned herein in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, or 50% versus a subject in which the methods of the present invention have not been practiced.

As used herein, the terms "prevent", "preventing" and "prevention" have their ordinary and customary meanings, and include one or more of, stopping, averting, avoiding, alleviating or blocking. Prevention means stopping by at least about 95% versus a subject to which the prevention has not been administered. Preferably, the stopping is about 100%, about 99%, about 98%, about 97%, about 96% or about 95%. The results of the prevention may continue for a period of days (such as 1, 2, 3, 4, 5, 6 or 7 days), weeks (such as 1, 2, 3 or 4 weeks) or months (such as 1, 2, 3, 4, 5, 6 or more months).

In each of the methods of the present invention, a "therapeutically effective amount" of a treatment, preventative agent, LBP or other active agent is administered to a subject. The effective amount these "active substances" will vary between subjects and the identity of the disease or condition being treated or prevented. However, the effective amount is one that is sufficient to achieve the aim or goal of the method.

While the active substances may be administered directly to a subject, the methods of the present invention are preferably based on the administration of a pharmaceutical formulation comprising one or more of the active substances and a pharmaceutically acceptable carrier or diluent. Thus, the invention includes pharmaceutical formulations comprising one or more of the active substances defined herein and a pharmaceutically acceptable carrier or diluent.

Pharmaceutically acceptable carriers and diluents are commonly known and will vary depending on the particular active substance being administered and the mode of administration. Examples of generally used carriers and diluents include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising the active substances will typically have been prepared and cultured in the absence of any non-human components, such as animal serum (e.g., bovine serum albumin).

Pharmaceutical formulations comprising one or more active substances may be administered to a subject using modes and techniques known to the skilled artisan. Characteristic of the diseases and conditions defined herein may make it more amenable to treatment and prevention using colonic delivery of active substances, i.e., targeted delivery of active substances to the lower GI tract, e.g., the large intestine or colon. Other modes of delivery include, but are not limited to, oral, anal, via intravenous injection or aerosol administration. Other modes include, without limitation, intradermal, subcutaneous (s.c., s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids).

Depending on the means of administration, the dosage may be administered all at once, such as with an oral formulation in a capsule or liquid, or slowly over a period of time, such as with an intramuscular or intravenous administration.

The amount of active substances, alone or in a pharmaceutical formulation, administered to a subject is an amount effective for the treatment or prevention of the target disease or condition.

Example 1—Intestinal Barrier Maturation in Very Low Birthweight Infants: Relationship to Feeding and Antibiotic Exposure Methods
A. Subjects All admissions to the University of Maryland Medical Center and Mercy Medical Center NICUs who were 240/7-326/7 weeks gestation<4 days of age were screened for study eligibility and parental consent of eligible subjects was obtained (ClinicalTrials.gov: NCT01756040). The institutional review boards of both institutions approved the study. Exclusion criteria included nonviability or planned withdrawal of life support; triplet or higher order multiples; severe asphyxia (Apgar score<3 at 5 minutes and cord pH<7.0); lethal chromosomal abnormalities; cyanotic congenital heart disease; intestinal atresia or perforation; abdominal wall defects; significant gastrointestinal dysfunction (e.g. heme-positive stools, abdominal distension (girth>2 cm baseline) or bilious emesis/aspirates, and infants with galactosemia or other forms of galactose intolerance. Before study procedures, a complete physical examination including vital signs, weight, height, and head circumference was performed. Demographic, clinical, and adverse events data were collected from the medical record.

Both participating clinical centers used the same standardized feeding protocol. Feeds were initiated between the first and fourth days of life depending on clinical stability. After initial feeds of 10 mL/kg expressed breast milk or 20 kcal/oz preterm formula daily for 3-5 days, feedings were advanced by 20 mL/kg/d until 100 mL/kg/d was reached. Subsequently, caloric density was advanced to 24 kcal/oz before increasing feeding volume by 20 mL/kg/d to 150 mL/kg/d. Feedings were held or discontinued for signs of feeding intolerance, such as abdominal distension, gastric residuals, or hematochezia, or for clinical deterioration.

B. Lactulose Rhamnose Sugar Absorption Test and Sample Collection

On each of the three study days (days 1, 8+2, and 15+2), participants received 1 mL/kg La/Rh solution (8.6 g of lactulose (Cumberland Pharmaceuticals, Nashville, TN)+140 mg of rhamnose (Saccharides, Inc., Calgary, Alberta, Canada)/100 mL) by nipple or by gavage via a clinically indicated orogastric tube (Rouwet et al., 2002). A minimum of 2 mL of urine was collected over a 4-hour period after the La/Rh dose was administered, with cotton balls placed in the infants' diaper. The total urine volume recorded included the volume extracted from the cotton balls in addition to the estimated volume of urine that leaked into the diaper determined by the diaper weight. The test was repeated the next day if <2 mL urine was collected. If there were signs of feeding intolerance (increased abdominal girth>2 cm, heme-positive stools, or gastric residuals), the sugar solution administration was either delayed until resolution of symptoms within the study four day window for each time-point or not done. Serum (total 0.5 mL) was collected by heel stick 90-120 minutes after La/Rh dosing to measure La/Rh (Haase et al. 2000) and serum zonulin. A stool sample (~1 g) was collected within 8 hours of the sugar probe dosing for A1AT analysis. Urine, serum, and stool samples were stored at −80° C. until analysis. The amount of lactulose and rhamnose in each sample was measured using high-performance liquid chromatography and adjusted for urine volume (Hilsden et al., 1996). The fractional urinary excretion of lactulose and rhamnose was calculated as the ratio of the total urinary excretion of each sugar probe to the total oral dose of the probe. For each subject, the lactulose/rhamnose ratio (La/Rh ratio) was calculated as the fractional excretion of lactulose divided by that of rhamnose (Mishra et al., 2012). A La/Rh ratio of >0.05 was considered indicative of increased IP (Beach et al., 1982).

C. Serum Zonulin Western Blot

Serum samples (70 mg per well) were run under non-denaturing conditions on 4%-20% Tris-Glycine gels (Invitrogen, Waltham, Massachusetts). Protein was transferred onto a PVDF membrane (Millipore, Billerica, Massachusetts) and probed with 1.5 mg/mL mouse monoclonal zonulin antibody (Bio-Rad, Hercules, California). Bands were detected with Alexa Flor 680 conjugated goat anti-mouse IgG antibodies (ThermoFisher, Waltham, Massachusetts). Bands were visualized and densitometry was measured using Image Studio software (LICOR Biosciences, Lincoln, Nebraska). All samples were normalized to a healthy term control reference sample run separately on each gel.

D. Stool A1AT ELISA

Stool samples diluted 1:250 according to the manufacturer's protocol were analyzed by double sandwich LISA (Eagle Biosciences, Nashua, New Hampshire) and results expressed as micrograms per gram of stool.

E. Statistical Analysis

The La/Rh ratio, serum zonulin, and stool A1AT data are represented as the mean and SD at each of the three time points. Categorical data were compared using the $\chi 2$ test and continuous data were compared with the Student t test. To quantify the association between urine La/Rh ratio, serum zonulin, and stool A1AT, Pearson correlation coefficients between the gold standard urinary La/Rh ratio and each of the other IP measures were calculated. IP patterns were differentiated using cluster analysis based on Ward minimum variance method, as implemented in SAS 9.3 (SAS Institute, Cary, North Carolina).

Results

Forty-four subjects were enrolled over an 18-month period from Apr. 15, 2013, to Oct. 15, 2014, and 43 subjects received≥1 dose of sugar solution. Demographic characteristics of the participants are represented in Table 1. Because there was interest in the maturation of intestinal barrier function in the extremely low gestational age (GA) infants, the data was analyzed for the entire cohort and stratified by GA≤28 weeks (n=12) and GA>28 weeks (n=31). The GA strata were similar in sex and race composition and obstetrical factors. However, feeding was delayed and antibiotic exposure more common and for longer durations in the less mature infants (GA≤28 weeks). There was a trend toward higher exclusive breast milk feedings in the less mature infants. No subject developed NEC during their neonatal intensive care unit stay.

TABLE 1

Study cohort clinical variables stratified by GA*

| Variables | Total cohort (n = 43) | GA ≤28 wk (n = 12) | GA >28 wk (n = 31) | P value |
|---|---|---|---|---|
| Sex (male) | 23 (53) | 8 (67) | 15 (52) | .33 |
| Race (African American) | 23 (55) | 8 (67) | 15 (48) | .33 |
| GA (wk) | 30 ± 2.3 | 26.6 ± 1.0 | 31.3 ± 1.0 | <.0001 |
| Birth weight (g) | 1336 ± 421 | 862 ± 94 | 1519 ± 348 | <.0001 |
| POL | 17 (40) | 7 (58) | 10 (32) | .17 |
| Duration ROM (hr) | | | | 1.0 |
| <1 | 19 (44) | 6 (50) | 13 (42) | |
| 1-72 | 18 (42) | 5 (42) | 13 (42) | |
| >72 | 5 (12) | 1 (8) | 4 (13) | |
| Unknown | 1 (2) | 0 | 1 (3) | |
| PPROM | 13 (30) | 4 (33) | 9 (29) | 1.0 |
| Pre-eclampsia | 9 (21) | 4 (33) | 5 (16) | .24 |
| Antenatal corticosteroids | 36 (84) | 11 (92) | 25 (81) | .65 |
| Clinical chorioamnionitis | 2 (5) | 0 | 2 (6) | 1.0 |
| Maternal antibiotics | 29 (67) | 6 (50) | 23 (74) | .16 |
| Cesarean delivery | 31 (72) | 8 (67) | 23 (74) | .71 |
| Day first enteral feeding | | | | .17 |
| 1 | 19 (44) | 5 (42) | 14 (45) | |
| 2-3 | 17 (40) | 3 (25) | 14 (45) | |
| ≥4 | 7 (16) | 4 (33) | 3 (10) | |
| Day first full feeding | | | | .0002 |
| 1-7 | 8 (19) | 0 | 8 (26) | |
| 8-14 | 20 (47) | 2 (17) | 18 (58) | |
| ≥15 | 15 (35) | 10 (83) | 16 (5) | |
| Exclusive breast milk | 25 (58) | 10 (83) | 15 (48) | .08 |
| Days on antibiotics | | | | .0019 |
| None | 8 (19) | 0 | 8 (26) | |
| 1-3 | 14 (33) | 1 (8) | 13 (42) | |
| ≥4 | 21 (49) | 11 (92) | 10 (32) | |

POL, preterm onset of labor; PPROM, preterm premature rupture of membranes; ROM, rupture of membranes.
*Data are expressed as n (%) or mean ± SD.

Figure 2:
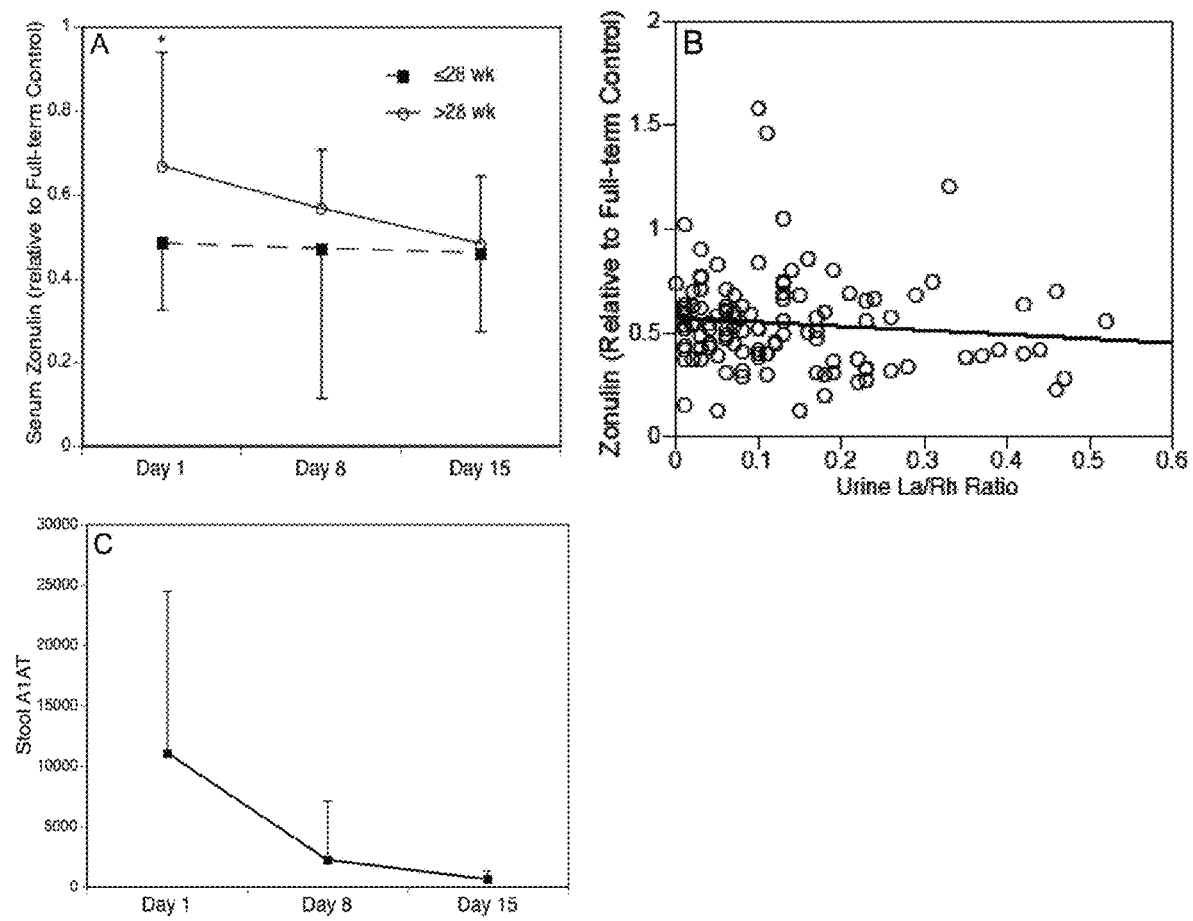
FIG. 2. Alternative measures of IP. A, Serum zonulin expressed relative to a healthy term control by GA strata and study time points. B, Serum zonulin/urinary La/Rh ratio correlation. C, Fecal AlAT concentration (µg/g stool). Data are expressed as mean±SD or present. *P<.05.

As shown in FIG. 1A, on average IP was increased on study day 1, decreased over 2 weeks, but remained higher in infants born at ≤28 weeks of gestation compared with IP in infants born at >28 weeks of gestation (P=.015, study day 8). Only one-third of infants≤28 weeks of gestation developed normal intestinal barrier function (La/Rh<0.05) by study day 15 (FIG. 1B). A cluster analysis of 35 subjects who had urine samples successfully collected at all 3 time points revealed that there were 3 distinct patterns of IP during the first 2 weeks of life (cluster 1, normal maturation: n=20 [57%]); cluster 2, decrease IP during the first week and subsequent substantial increase: n=5 [14%]); and cluster 3, delayed maturation: n=10 [29%]) (FIG. 1C). Further analysis of factors associated with abnormal IP patterns (clusters 2 and 3) revealed trends toward a more prolonged duration of antibiotic exposure (≥4 days) (10/15 [67%] vs 7 [35%]; P=0.092) and delayed initiation of feeding (≥4 days) (5 [33%] vs 1 [5%]; P=064) in infants with abnormal maturation patterns compared with infants with normal maturation. There was a trend towards greater co-exposure to prolonged antibiotics and delayed feeding of >4 days in infants with abnormal maturation patterns than in infants with normal maturation (4/15 [27%] vs 1/20 [5%]; P=.141). Compared with infants fed preterm formula with or without expressed breast milk (n=18), infants fed exclusively with expressed breast milk (n=25) demonstrated more rapid improvement in intestinal barrier function on study day 15 (P=.0088) (FIG. 1D). Gestational and postnatal age-dependent changes in serum zonulin relative to a healthy full-term control infant are represented in FIG. 2A. Although serum zonulin levels were low relative to a healthy full-term control, levels were significantly higher in infants born at >28 weeks of gestation compared with infants born at ≤28 weeks of gestation on day 1 (P=.012). Serum zonulin did not correlate with urinary La/Rh ratios (FIG. 2B). Although there was considerable variability in stool AlAT concentrations on study day 1, stool AlAT decreased over time similar to urinary La/Rh, indicating maturation of the intestinal barrier (FIG. 2C). Although serum lactulose/rhamnose has been measured in serum of infants>4 months of age (Haase et al., 2000), rhamnose was undetectable in serum samples from the cohort collected 90-120 minutes after sugar solution dosing, so the La/Rh ratio could not be calculated (data not shown).

These data suggest that intestinal barrier function is impaired in preterm infants and maturation depends on gestational and postnatal age, and may be altered by feeding and antibiotic exposures, with a maturational effect of breast milk feeding. Although intestinal barrier function improved over time in 57% of subjects, IP increased during the second week or maturation was delayed in the remaining infants.

Example 2—Microbial Biomarkers of Intestinal Barrier Maturation in Preterm Infants Methods A. Participants and Intestinal Permeability Measurement This study was approved and carried out in accordance with the recommended protocol by the institutional review boards of the University of Maryland and Mercy Medical Center. All subjects have obtained written informed parental consent in accordance with the approved protocol. All methods were performed in accordance with the relevant guidelines and regulations. Thirty-eight preterm infants 240/7-326/7 weeks GA were enrolled within 4 days after birth and received 1 ml/kg of the non-metabolized sugar probes lactulose (La) (marker of intestinal paracellular transport)/rhamnose (Rh) (marker of intestinal transcellular transport) (8.6 g La+140 mg Rh/100 mL) enterally within 24 h of enrollment on study day 1, and subsequently on study day 8+2 and 15+2. La/Rh was measured by high-pressure liquid chromatography (HPLC) in urine collected over a 4 h period following administration of the sugar probes as previously described (Saleem et al., 2017). High or low intestinal permeability was defined by a La/Rh>0.05 or ≤0.05 respectively, as validated and applied previously (Saleem et al., 2017). Postmenstrual age (PMA) at each study time point was calculated as gestational age at birth plus postnatal age as defined previously (Grier et al., 2017). Fecal samples (~1 g) were collected at the same time as the dual sugar administration and stored immediately in 2 ml of RNAlater (QIAGEN). Urine and fecal samples were archived at −80° C. until processed. A standard feeding protocol was used for all preterm participants. To compare microbiota of infants at different growth phases (Mshvildadze et al., 2008; Unger et al., 2015), 16 samples from older term infants at phase II/III (6-24 months old) from a previous study (Sellitto et al., 2012) were included in the comparative analyses.

B. Stool Nucleic Acid Extraction and Sequencing

DNA was extracted from all samples as previously reported (Ravel et al., 2011). Briefly, a 500 ml aliquot of fecal material mixture was homogenized and carefully washed twice in PBS buffer. Enzymatic lysis using mutanolysin, lysostaphin and lysozyme was performed, followed by proteinase K, SDS treatment and bead beating. DNA purification from lysates was done on a QIAsymphony automated platform. PCR amplification of the V3-V4 variable region of 16S rRNA gene was performed using dual-barcoded universal primers 319F and 806R as previously described (Fadrosh et al., 2014). High-throughput sequencing of the amplicons was performed on an Illumina MiSeq platform using the 300 bp paired-end protocol. Metagenomic sequencing libraries were constructed from the same DNA using Illumina Nextera XT kit according to the manufacturer recommendations. Stool specimen was advised to be collected within the stool mass as much as feasible from diaper to avoid frequent air exposure. The stool sitting time is 0-3 h and was collected during diaper change every 3 h in NICU. Stool specimen were stored immediately in RNALater that stabilizes and protects the integrity of RNA to minimize the need to immediately process or freeze specimen (Gorokhova, 2005). The use of metatranscriptome in microbiome study is still a very young field, intensive evaluations such as RNA consistency over time in stool diaper collection are needed for future validation. Total RNA was extracted from 250 ml of stool homogenized in RNALater. Briefly, lysis was performed by bead beating using the FastPrep lysing matrix B protocol (MP Biomedicals), followed with two rounds of protein cleanup using phenol-chloroform in 5PRIME heavy phase lock tubes (QuantaBio) and precipitation of total nucleic acids using isopropanol. Genomic DNA was removed using TURBO DNase (Ambion). Ribosomal RNAs were depleted using the Gram-negative and Human/mouse/rat Ribo-Zero rRNA Removal kits (Epicentre Technologies). The resulting RNA was used for library construction using Illumina TruSeq stranded mRNA library preparation kit according to the manufacturer's recommendations. Quantification of the constructed RNA libraries was performed on an Agilent Bioanalyzer using the DNA 1000 Nano kit. Both metagenome and metatranscriptome samples were sequenced on an Illumina HiSeq 4000 instrument at the Genomics Resource Center (GRC), Institute for Genome Sciences, University of Maryland School of Medicine using the 150 bp paired-end protocol.

Bioinformatics Analysis of Intestinal Microbiota

Sequencing read quality assessment was performed using strict criteria to ensure high quality and complete sequences of the amplified the V3-V4 regions of the 16S rRNA gene, according to the procedures, programs and citations, and parameters described previously (Fadrosh et al., 2014). Briefly, a sequence read was trimmed at the beginning of a 4 bp sliding window if the average quality score was less than Q15. The sequence read was then assessed for length and retained if it was at least 75% of its original length. The paired-end reads were assembled to take advantage of the ~90 bp overlapping region. These sequences were further de-multiplexed the sequence reads by individual samples. Additional quality filtering was applied that removed sequences with more than one mismatch in the barcode sequence tag or with ambiguous nucleotide. Taxonomic assignments were performed on each sequence using the Ribosomal Database Project trained on the Greengene database (Aug 2013 version), using 0.8 confidence values as cutoff. Clustering taxonomic profiles was performed as previously described (Ravel et al., 2011). The number of clusters was validated using gap statistics implemented in the cluster package in R (Maechler, 2016) by calculating the goodness of clustering measure. Within-sample diversity was estimated using both observed OTUs to measure community richness and Shannon diversity index. Linear discriminant analysis (LDA) effect size (LEfSe) analysis (Segata et al., 2011) was used to identify fecal phylotypes that could explain the differences between infants with low or high La/Rh ratio on different sampling days. For LEfSe, the alpha value for the non-parametric factorial Kruskal-Wallis (KW) sum-rank test was set at 0.05 and the threshold for the logarithmic LDA model (Fisher, 1936) score for discriminative features was set at 2.0. An all-against-all BLAST search in multi-class analysis was performed. Balance tree analysis was applied as implemented in Gneiss, and trees were generated using Ward hierarchical clustering of abundance profiles. Balance was computed as the isometric log ratio of mean abundances at each bifurcating node in the tree, to characterize the "flow" of changes in the abundance of a group of correlated bacteria in a microbial community (Morton et al., 2017). Multivariate response linear regression on the calculated balances was performed, and multiple factors were included as covariates, including antibiotics use, maternal antibiotics use, delivery mode, preterm premature rupture of membranes, feeding pattern and source, intestinal permeability, birthweight, gender, ethnicity, GA and PMA. Leave-one-variable-out approach was used to calculate the change in R square to evaluate the effect of a single covariate on the community. Tenfold cross validation was performed to mitigate the common overfitting issues in statistical modeling.

D. Statistical Analysis

An adaptive spline logistic regression model implemented in spmrf R package (Faulkner and Minin, 2018) was adapted to determine the associations between intestinal permeability and relative abundance of bacterial phylotypes. This model is a locally adaptive non-parametric fitting method that operates within a Bayesian framework, which uses shrinkage prior Markov random fields to induce sparsity and provides a combination of local adaptation and global control (Faulkner and Minin, 2018). The analysis was performed on the phylotypes present in at least 15% of all samples, and the effect size was defined as the difference between the extreme values of the probability of intestinal permeability index. Given that there were multiple samples collected from each subject, this model takes into consideration of the dependencies among samples within a subject. Bayesian goodness-of-fit p-value implemented in R package rstan (Team, 2018) was used to access the significance of the association between phylotypes and metadata including antibiotics use, maternal antibiotics use, delivery mode, PPROM, feeding pattern, intestinal permeability, birthweight, gender, ethnicity, gestational age, and postmenstrual age. Data not shown includes R code implementation of the model. Random forest supervised machine learning scheme implemented in R package randomForest was further adapted (Liaw and Wiener, 2002) to test the predictability of the phylotypes of microbial community on intestinal permeability. The top 15 phylotypes relative abundance with highest mean decrease gini index importance measure, were fitted to a random effect logistic regression model of intestinal permeability that was defined as a dichotomous variable high (La/Rh>0.05) or low (La/Rh≤0.05). The relative abundances of phylotypes were centered to the mean and scaled by standard deviation to apply to the model to normalize relative abundances. Data not shown includes R code implementation of the model.

E. Intestinal Microbiome Analyses

Metagenomic and metatranscriptomic sequence data were preprocessed using the following steps: (1) human sequence reads and rRNA LSU/SSU reads were removed using BMTagger v3.101 (Rotmistrovsky and Agarwala, 2011) using a standard human genome reference (GRCh37.p5) (Church et al., 2011); (2) rRNA sequence reads were removed in silico by aligning all reads using Bowtie v1 (Langmead et al., 2009) to the SILVA PARC ribosomal-subunit sequence database (Quast et al., 2013). Sequence read pairs were removed even if only one of the reads matched to the human genome reference or to rRNA; (3) the Illumina adapter was trimmed using Trimmomatic (Bolger et al., 2014); (4) sequence reads with average quality greater than Q15 over a sliding window of 4 bp were trimmed before the window, assessed for length and removed if less than 75% of the original length; and (5) no ambiguous base pairs were allowed. The taxonomic composition of the microbiomes was established using MetaPhlAn version 2 (Segata et al., 2012). Normalization using Witten-Bell smoothing was performed since metatranscriptomes are a random sampling of all expressed genes and transcripts can be identified that correspond to genes not represented in the metagenome, particularly for low abundance species that were metabolically active (Franzosa et al., 2014). The relative expression of a gene in a sample was calculated by normalizing the smoothed value of the expression level in the metatranscriptome by the smoothed value of the corresponding gene abundance in the metagenome, as suggested previously (Franzosa et al., 2014, 2015). Correlation plots were generated using R corrplot package (Wei and Simko, 2017). Genotypic variation of *Escherichia coli* was performed through reconstructing MLST loci-sequences from metagenomes using metaMLST program (Zolfo et al., 2017). The resulting STs were visualized to show related genotypes of *E. coli* strains on a minimum spanning tree computed by a goeBURST algorithm (Francisco et al., 2009) implemented in PHYLOViZ (Nascimento et al., 2017).

Results

A. Intestinal Barrier Maturation Correlates With Increased Microbiota Biodiversity Over the First Two Weeks of Life Study days were defined as day 1, day 8±2 and day 15±2 with the first study day within 4 days after birth. Of 43 subjects<33 weeks gestation who were enrolled in the study, stools samples were available from 38. The demographic, obstetric, and neonatal characteristics for included subjects are summarized in Table 2. The study cohort has on average birthweight at 1,386±404 g and gestational age at 29.9±2.2 weeks. The mean IP measurement of this cohort including all timepoints is 0.10±0.12 and 52.5% of the sampling points have elevated IP. The microbiota of 64 fecal samples were successfully characterized by high-throughput sequencing of the V3-V4 variable regions of 16S rRNA genes. A total of 422,444 high-quality amplicon sequences was obtained, corresponding to 10,544 (±4,029) sequences per sample with an average length of 428 bp.

TABLE 2

Characteristics of study subjects
(preterm infants <33 weeks gestational age)

|  | N | % |
|---|---|---|
| Ethnicity |  |  |
| African American | 22 | 57.9 |
| Asian | 3 | 7.9 |
| White | 12 | 31.6 |
| Others | 1 | 2.6 |
| Gender |  |  |
| Female | 17 | 44.7 |
| Male | 21 | 55.3 |
| Delivery route |  |  |
| Cesarean | 26 | 68.4 |
| Vaginal | 12 | 31.6 |
| Gestational age/ | 29.9 ± 2.2/ |  |
| Postmenstrual age* (weeks) | 31.4 ± 2.3 |  |
| Birth weight | 1.386 ± 404 |  |
| <1500 g | 21 | 55.3 |
| >1500 g | 17 | 44.7 |
| Intestinal permeability** | 0.104 ± 0.123 |  |
| High | 31 | 52.5 |
| Low | 28 | 47.5 |
| Antibiotic use |  |  |
| None | 7 | 18.4 |
| 1-3 days | 12 | 31.6 |
| >4 days | 19 | 50.0 |
| Day start breastmilk feeding |  |  |
| Day 1 | 17 | 44.7 |
| Day 2 or 3 | 15 | 39.5 |
| >Day 4 | 6 | 15.8 |
| Day reached full breastmilk feeding |  |  |
| <Day 7 | 5 | 13.2 |
| Day 8-14 | 15 | 39.5 |
| >Day 15 | 18 | 47.4 |
| Microbiota type*** |  |  |
| (most abundant species) |  |  |
| I (*Klebsiella pneumonia*) | 27 | 42.2 |
| II (*Staphylococcus epidermidis*) | 26 | 40.6 |
| III (*Escherichia coli*) | 11 | 17.2 |

*Postmenstrual age was calculated as gestational age at birth plus week of life (Grier et at., 2017).
** The low and high intestinal permeability category was defined by a La/Rh >0.05 or ≤0.05, respectively (Saleem et al., 2017).
***Microbiota type was defined based on clustering of taxonomic profiles using 16S rRNA gene amplicon in this study.

Figure 3:
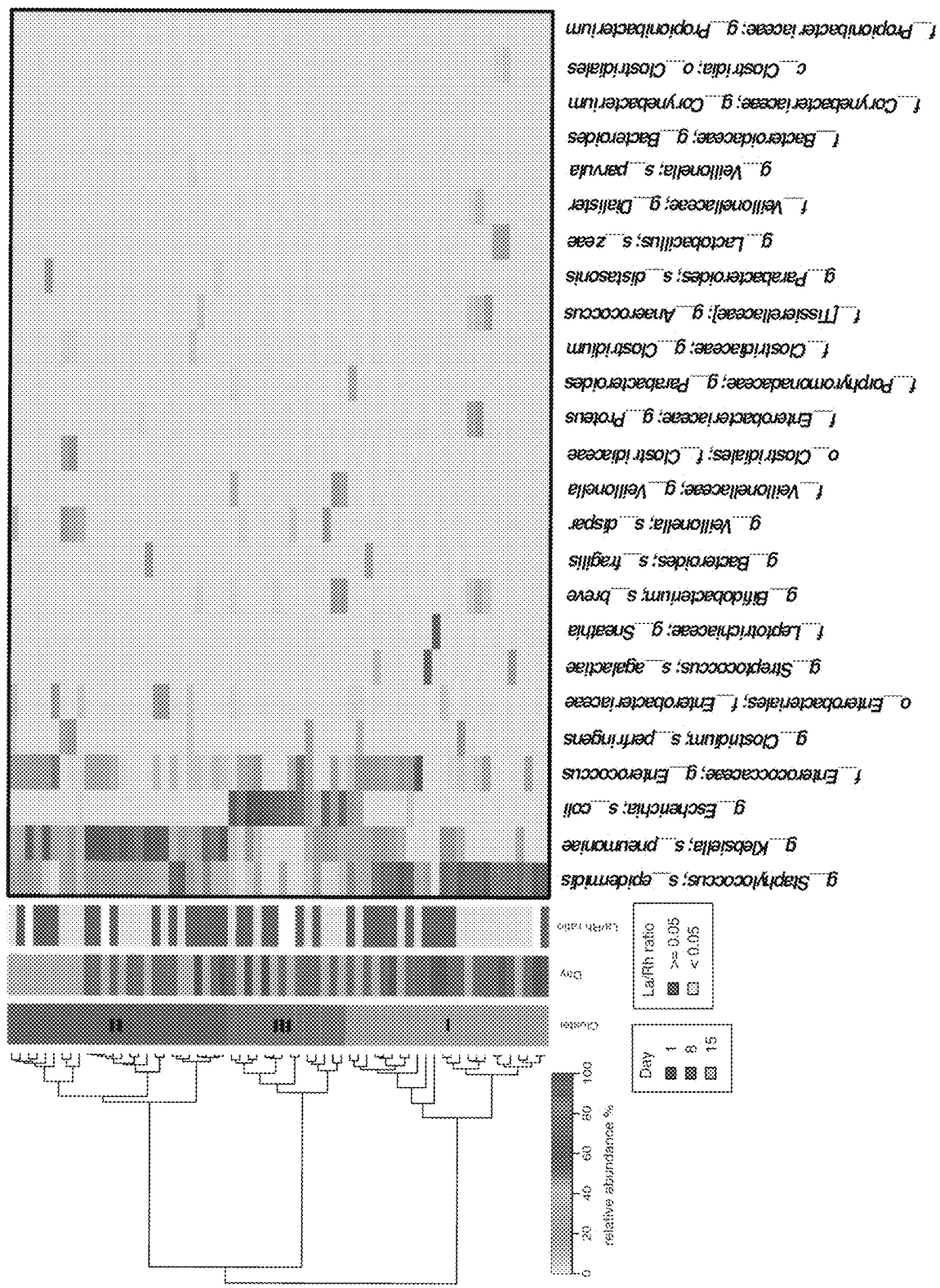
FIG. 3. Heatmap of the 50 most abundant intestinal bacterial taxa relative abundance in samples collected from 38 preterm infants enrolled in the study. The microbiota of 64 fecal samples were successfully characterized by high-throughput sequencing of the V3-V4 variable regions of 16S rRNA genes. The three sidebars indicate cluster, time, and intestinal permeability category, respectively. Ward linkage clustering was used to cluster samples based on their Jensen-Shannon distance calculated in vegan package in R (Oksanen et al., 2011). The samples with no IP assessment were included to generated the clusters. The low and high intestinal permeability category was defined by a La/Rh>0.05 or <=0.05 respectively (Saleem et al., 2017). Taxonomic profiling of corresponding metagenomes further resolved *Klebsiella* spp. to *Klebsiella pneumoniae*, *Enterococcus* spp. to *Enterococcus faecalis*, and *Bifidobacterium* spp. to *Bifidobacterium breve*.
Figure 4:
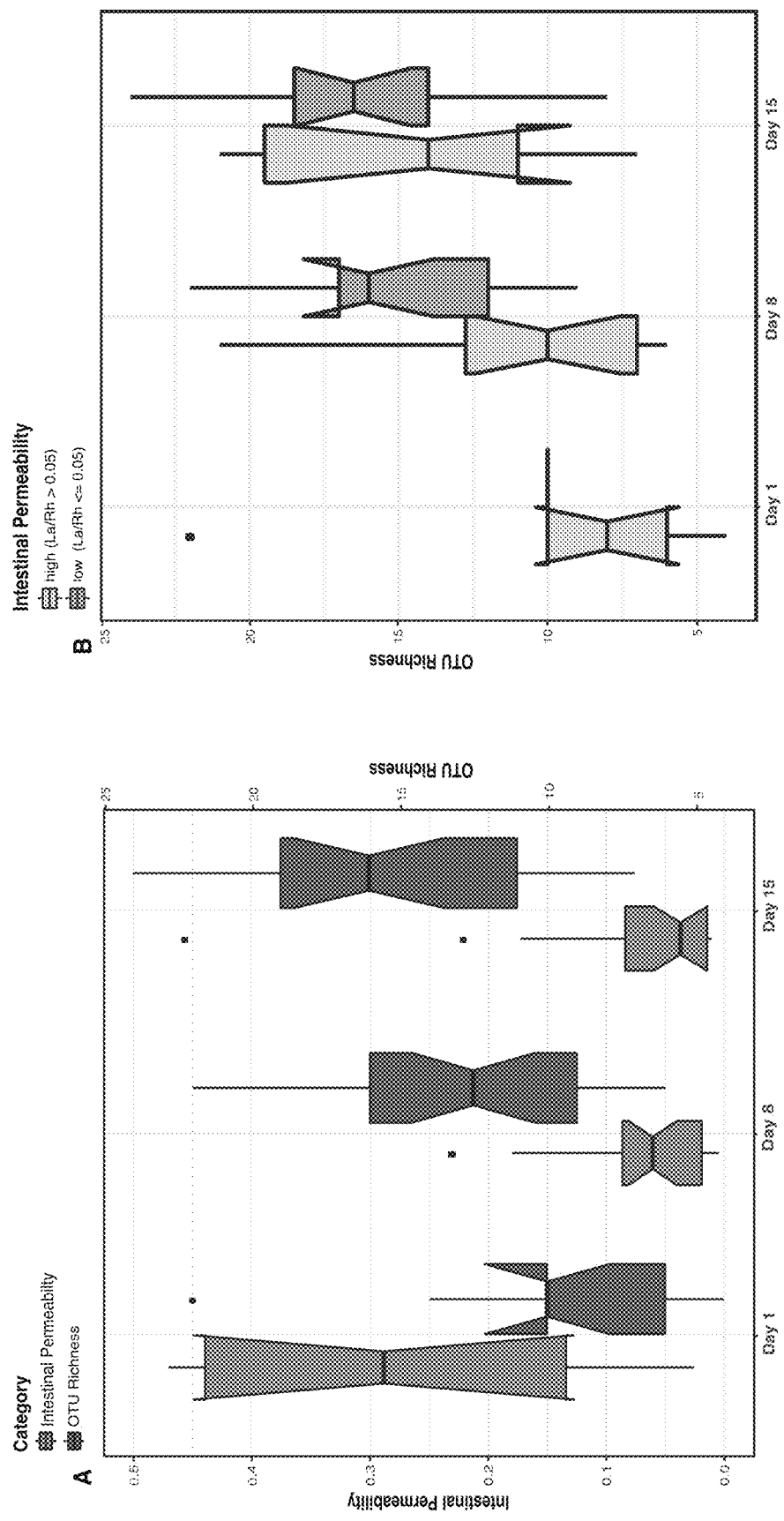
FIG. 4. Boxplots comparing levels of intestinal permeability and microbial community diversity at study days 1, 8, and 15 in a cohort of 38 preterm infants (<33 weeks gestational age). Intestinal permeability is measured by non-metabolized sugar probes lactulose (La) (marker of intestinal paracellular transport)/rhamnose (Rh) (marker of intestinal transcellular transport). Microbial community diversity was calculated by OTU (Operational Taxonomic Units) richness. Wilcoxon rank sum test and a false discovery rate of 5% was used in significance test. Median values and interquartile of the values were shown in box. A, Intestinal permeability (p-value=0.002) and community diversity at the three study time points (p-value=0.02). B, Community diversity (p-value<0.001) in infants with low and high intestinal permeability defined by a La/Rh>0.05 or ≤0.05 respectively (Saleem et al., 2017).

The top 25 most abundant phylotypes are shown in FIG. 3. Taxonomic profiles of all samples were clustered into three distinct groups according to similarities in community composition and structure. *Klebsiella* spp., *Staphylococcus epidermidis*, and *Escherichia coli* dominated cluster I, II, and III, respectively. Data not shown includes La/Rh ratio and taxonomic profile of each sample. Taxonomic profiling of corresponding metagenomes further resolved *Klebsiella* spp. to *Klebsiella pneumoniae*, *Enterococcus* spp. to *Enterococcus faecalis*, and *Bifidobacterium* spp. to *Bifidobacterium breve*. Taxonomic profiles of stool samples from infants at 6-24 months of age born at term, or phase II/III as defined previously (Mackie et al., 1999; Mshvildadze et al., 2008; Unger et al., 2015), clustered together in a different and more diverse cluster (data not shown). Rapid decrease in IP over the 2-week observation period indicates intestinal barrier function maturation (p-value=0.002), which is correlated with a significant increase in community diversity (p-value=0.02) (FIG. 4A); while delayed increase in community diversity was associated with persistence of high intestinal permeability (p-value<0.001) (FIG. 4B). The results indicated that preterm infant intestinal barrier maturation correlates with increased fecal microbiota biodiversity and a change in microbiota composition and structure.

B. Subject Variation, Postmenstrual Age, and IP Explain Most of the Variation in Intestinal Microbiota A multivariate response linear regression was employed on the "balance" of microbial community and the effect of covariates of demographic, obstetric, and neonatal factors was evaluated on the microbiome using Gneiss (Morton et al., 2017). Covariates of antibiotics use, maternal antibiotics use, delivery mode, preterm premature rupture of membranes (pPROM), feeding pattern, IP, birthweight, gender, ethnicity, gestational age (GA) and postmenstrual age (PMA) were included in the analysis. Multivariate response linear regression was fitted on the "balance", or isometric log ratio of mean abundances of a group of phylogenetic correlated bacteria in a microbial community (Lin et al., 1999), to calculate the change of balance on the whole community with respect to a single covariate. Model was represented: $\vec{y}=\beta 0+\beta_{Subject}X_{subject}+\beta_{sex}X_{sex}+\beta_{GA}X_{GA}{}^+\ldots$, where y represents the matrix of balances, βi represents a vector of coefficients for covariate i and math:vec{X_i} represents the measures for covariate i. * Evaluated covariates include antibiotics use, maternal antibiotics use, delivery mode, PPROM, feeding patterns, IP (intestinal permeability), birthweight, gender, ethnicity, gestational age (GA) and postmenstrual age (PMA, or corrected GA). Difference in $R^2$ of the model (y-axis) was used to access the effect of covariates on overall variance of microbial community. Subject, PMA, and IP were shown to have the most explanatory covariates, together they explained 63.4% of the observed variation of the intestinal microbial community composition observed in the cohort (FIG. 5A).

The predicted points lie within the same region as the original communities and the residuals have roughly the same variance as the predictions within +2, indicating the model is fitting the data well (data not shown). Overall the result indicates the microbial differences between subjects are large (R squared difference is 0.023+0.01), and the covariate with strongest effect was PMA (R squared difference is 0.044), suggesting that intestinal microbial composition has subject-to-subject difference and is development-dependent. IP correlated with the intestinal microbiota (R squared difference is 0.020), and its effect was lower than PMA and similar to the average among-subject effect.

Figure 5:
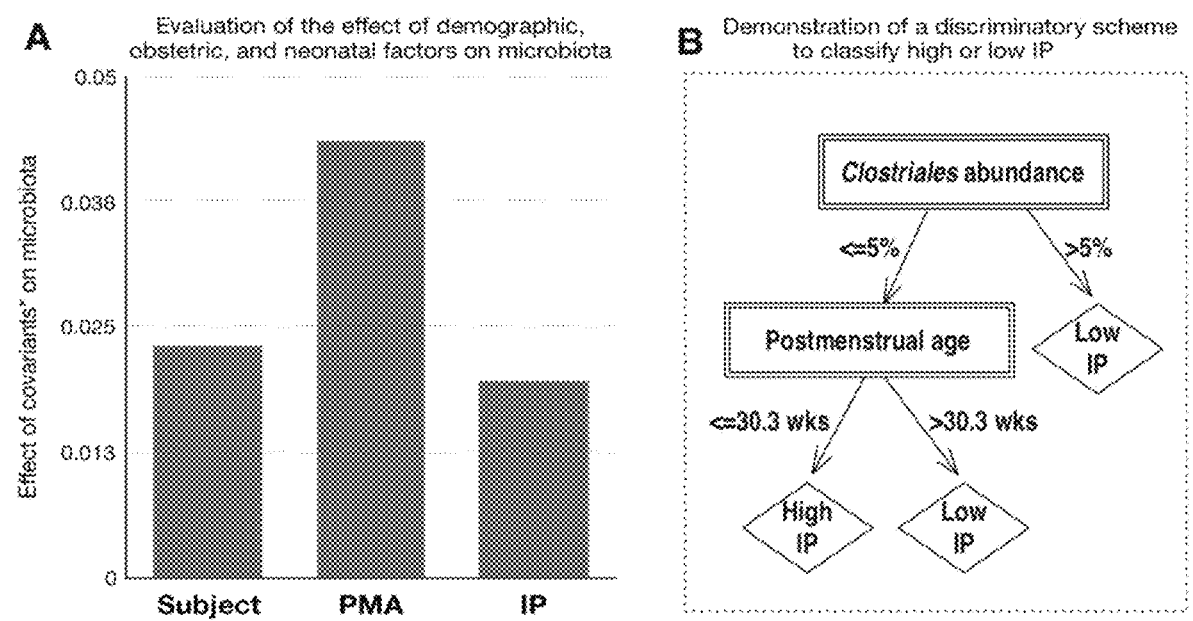
FIG. 5. A, Evaluation of the effect of demographic, obstetric, and neonatal factors as covariates on microbial community composition and structure. Difference in $R^2$ of the model (y-axis) was used to access the effect of covariates on overall variance of microbial community. Subject, PMA, and IP were shown to have the most explanatory covariates, together they explained 63.4% of the observed variation of the intestinal microbial community. B, Discriminatory scheme for high or low IP.

Supporting this postulate is the result from supervised machine learning modeling (Frank et al., 2004), in which the cohort was stratified into high (≥5%) and low (≤5%) Clostridiales abundance groups, that shows infants with early postmenstrual age (≤30.3wks) in the low Clostridiales group are most likely to have elevated IP (FIG. 5B). Interestingly, this discriminatory scheme boosts predictive accuracy to 86.1%, which is significantly higher than using PMA or Clostridiales abundance alone to identify an aberrant IP that have accuracies of 59.4% and 33.9%, respectively. Thus, a scheme comprising potentially strong predictors of poor IP and poor intestinal maturation in preterm infants has been identified.

Clostridiales Is Associated With Low Intestinal Permeability in Preterm Infants

Figure 6:
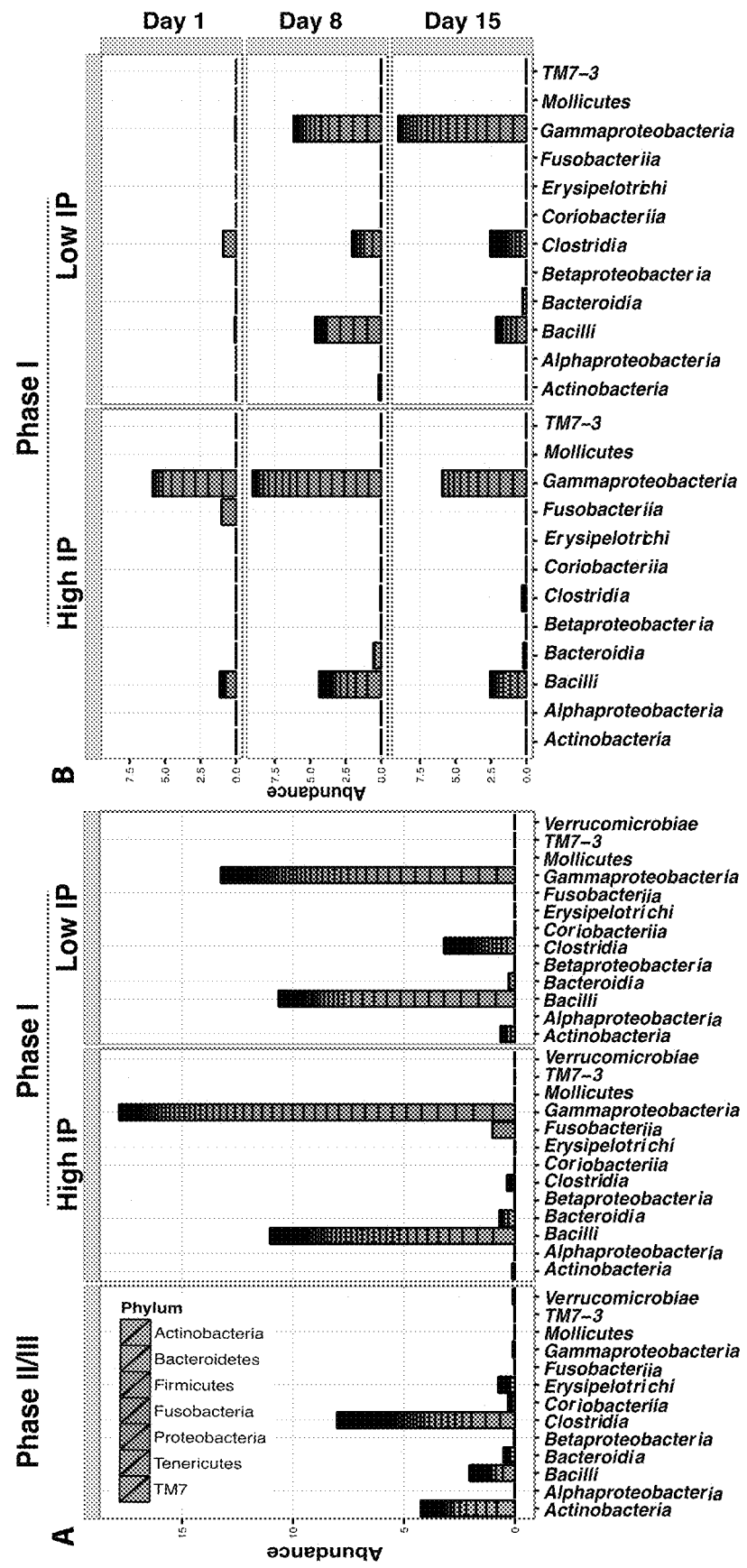
FIG. 6. Comparison of relative abundance of bacterial groups in stool samples associated with high and low IP (La/Rh) measurements. A, Cumulative abundance between phase II/III subjects (6-24 months of age) and phase I infants (within first 2 weeks of life) with high and low IP. B, Cumulative abundance at study day 1, 8, and 15 for phase I infants with high and low IP. C, Cumulative abundance at study day 1, 8, and 15 for phase I infants that had first day starting breastmilk feeding at day 1 or 2, or day 3 and later. D, The relative abundance of Clostridiales of each sampling point and the number of samples at study day 1, 8, and 15 for phase I infants with high or low IP. Bars represent the relative abundance of Clostridiales in each sample. Dotted line and solid line represent mean, and median relative abundance, respectively. Clostridiales was identified to be significantly discriminative with respect to the IP class (p-value=0.0002, logarithmic linear discriminant analysis (LDA) score is 4.996) using LDA effect size (LEfSe) analysis (Segata et al., 2011). The alpha threshold value for the pairwise non-parametric Kruskal-Wallis test was 0.05 and the threshold for the logarithmic LDA model score (Fisher, 1936) for discriminative features was 2.0. An all-against-all comparison in multi-class analysis was performed. The low and high IP category was defined by a La/Rh>0.05 or ≤0.05 respectively.
Figure 6:
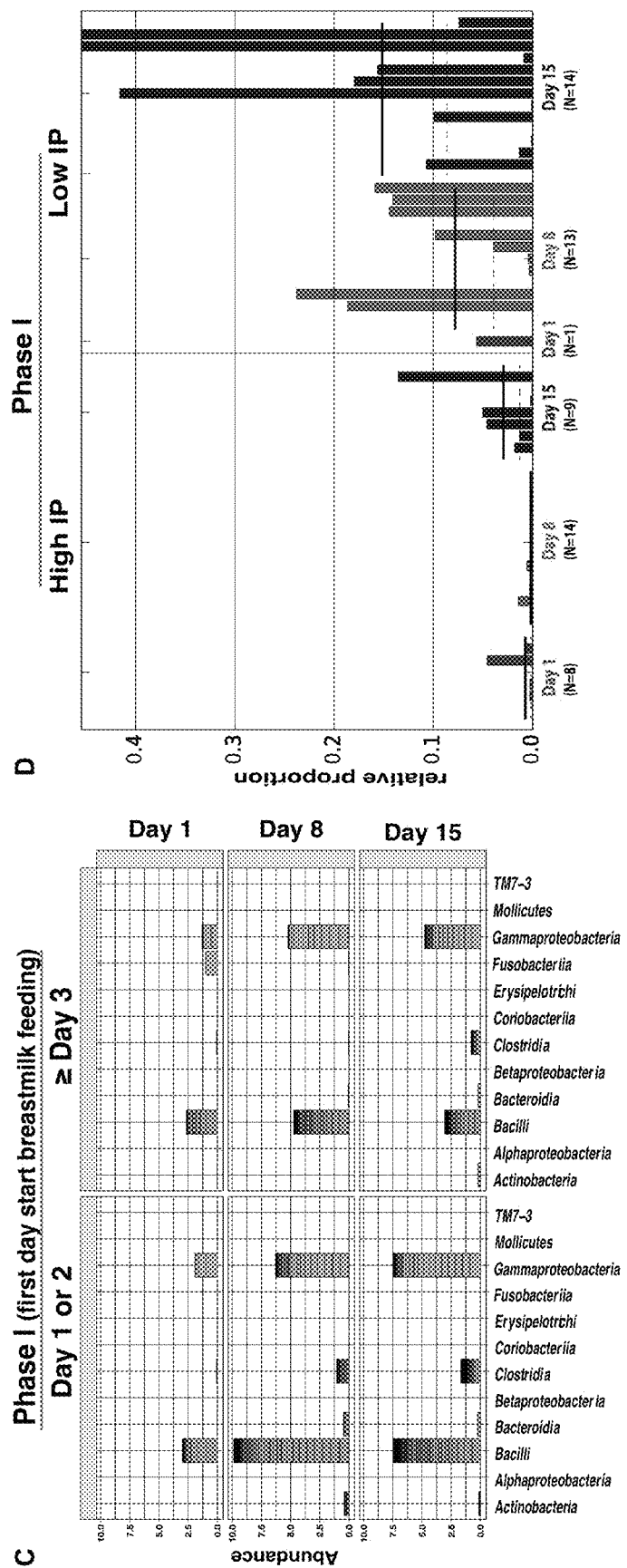

Comparative analysis of fecal microbiota with high (La/Rh≥0.05) and low IP (La/Rh<0.05) showed that Clostridia, the class containing the only order Clostridiales in this cohort, was significantly more abundant in samples with low IP compared to those with high IP (p-value=0.01) (FIGS. 6A,B). In particular, a progressive and significant increase in members of Clostridiales over the first 2 week after birth significantly associated with low IP (p-value=0.0002) as shown in FIG. 6D. The significance level was calculated based on all samples from the three time points. Based on Bayesian non-parametric adaptive smoothing models and subject-specific changes in relative abundance of Clostridiales at study day 1, 8, and 15, the results demonstrated: (1) at baseline study day 1 within 4 days of birth, the abundance of Clostridiales was low in subjects with either high or low IP; (2) however, in samples measures with low IP but not high IP, a significant increase in Clostridiales was observed that reached ~8% median and >20% maximal relative abundance at study day 8, and ~16% median and ~45% maximal relative abundance at study day 15; (3) on the other hand, in infants with persistently high IP (delayed maturation), members of Clostridiales was almost completely absent on study day 8 and no increase was observed from study day 1 to 8, and its abundance level on study day 15 was only at ~3% median and ~10% maximal relative abundance; (4) in infants 6-24 months old, Clostridiales is the most abundant taxonomic groups with >50% median and >85% maximal relative abundance (data not shown). Interestingly, for the subjects that started breastmilk feeding within the first 1 or 2 days, it also appears Clostridiales was progressively more abundant at the end of the first and second weeks. On the contrary for the subjects that started breastmilk feeding on study day 3 or later, the Clostridiales were less established (FIG. 6C), highlighting the impact of early breastmilk feeding on bacterial colonization that shapes intestinal community. Together, the results suggest preterm infants at birth have low abundance of Clostridiales, which became progressively and significantly more abundant only in the group with rapid progression of intestinal barrier maturation, while remained low in those with persistent high IP over the first 2 weeks of life.

The predictive power of microbiota composition was further calculated in classifying IP using random forest supervised machine learning scheme. The top 15 phylotypes with the highest mean decrease gini index importance measure (data not shown) were used to fit a random effect logistic regression model of IP, 4 of which were significantly associated with low IP (data not shown), including three members of the order Clostridiales, *Coprococcus* (p-value=0.004), Lachnospiraceae (p-value=0.007), *Veillonella dispar* (p-value=0.01), and *Bifidobacterium* (p-value=0.01) from the order of Bifidobacteriales. Interestingly, Bifidobacteriales was the second most abundant taxonomic groups in infants 6-24 months old, only lower than Clostridiales (data not shown).

Figure 7:
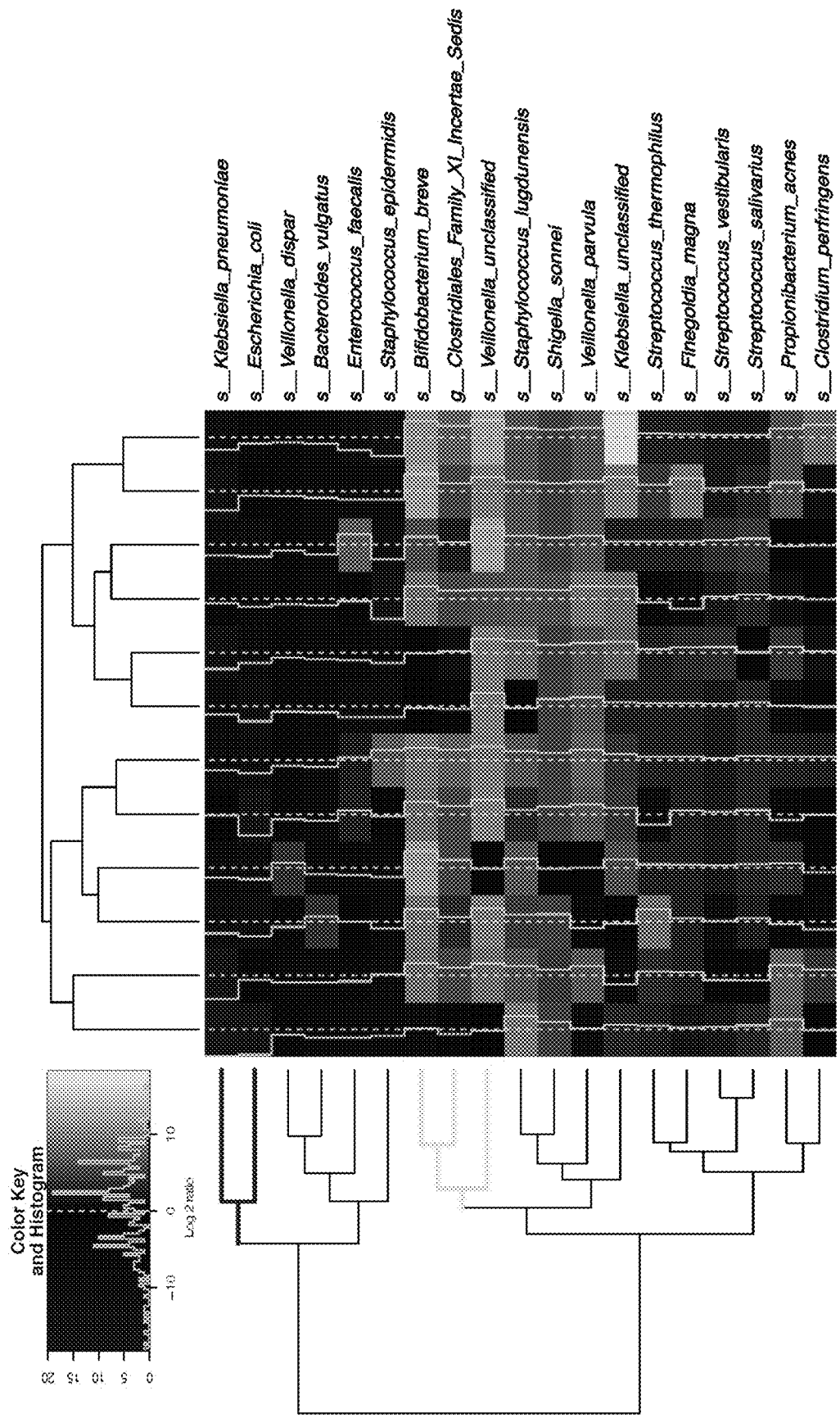
FIG. 7. Bacterial species transcriptional activity in preterm infant stools. Fecal samples are represented in columns and taxonomic composition quantified using MetaPhlAn (Segata et al., 2012) version 2 are shown in rows, both are organized by hierarchical clustering. Normalization using Witten-Bell smoothing was performed, and the relative expression of a gene in a sample was calculated by normalizing the smoothed value of the expression level in the metatranscriptome by the smoothed value of the corresponding gene abundance in the metagenome (Franzosa et al., 2014; Franzosa et al., 2015). Color scheme indicates an approximate measure of the species' clade-specific transcriptional activity (Franzosa et al., 2014). The colored branches show the clustering of bacterial species that are consistently transcriptionally active (yellow) or consistently transcriptionally inactive (blue) across samples.

D. Clostridiales and *Bifidobacterium* Are Highly Active Members of the Intestinal Microbiome The level of bacterial transcriptional activities was characterized by studying the suite of genes present and expressed in preterm infant intestinal microbiota. A total of 869 million metagenomics sequence reads (average of ~31.0 million sequence reads per sample) and 694 million meta-transcriptomic sequence reads (average of ~53.4 million sequence reads per sample) were obtained after quality assessment. FIG. 7 shows that *Bifidobacterium breve* (Actinobacteria), *Veillonella* and Clostridiales Family XI incerteae Sedis (Clostridiales) were the most transcriptionally active bacteria with high ratio of transcript abundances over gene abundances in all samples. Further, the levels of transcriptional activities of *Bifidobacterium breve* and Clostridiales Family XI incerteae Sedis were correlated with a spearman correlation of 0.89, suggesting these two taxonomic groups are either functionally dependent or co-regulated (data not shown). An increased abundance of both Clostridiales and Bifidobacteriales was observed through the transition from the first 2 weeks (phase I) to later age of 6-24 months (phase II/III) as further supporting their active contribution to the function of the GI microbiota after birth. Interestingly, Clostridiales and Bifidobacteriales were also the most abundant taxonomic groups in the intestinal microbiota of 6-24 months old infants (data not shown). Specifically, members of the family Clostridiales have an average abundance of 50±3% in phase II and III infants, compared to 0.1+0.4% in phase I infants. Bifidobacteriales have an abundance of 26±5% in phase II and III as opposed to 0.1+0.3% in phase I infants. Together with the previous observation that *Coprococcus* (Clostridiales), Lachnospiraceae (Clostridiales), *Veillonella dispar* (Clostridiales), and *Bifidobacterium* (Bifidobacteriales) are significantly associated with low IP, the results suggest the presence and more importantly the activity of bacterial members of Clostridiales and Bifidobacteriales are associated with improved intestinal barrier maturation. Conversely, the two Enterobacteriaceae species, *Klebsiella pneumoniae* and *Escherichia coli*, had low transcriptional activity despite their high relative abundance in the infant GI microbiota, questioning their functional contribution to the infant stool microbiota. Interestingly, Enterobacteriaceae and *Staphylococcus* are the most abundant bacterial taxa present in phase I infants but are rarely observed in phase II and III (data not shown).

E. Early Breast Milk Feeding and Shorter Duration Antibiotic Exposure Positively Correlates With Clostridiales Abundance and Activities The associations between intestinal microbiota and demographic, obstetric, and neonatal factors were also evaluated. Gneiss analysis suggests delivery mode, pPROM, gender, ethnicity, birthweight, maternal antibiotics use are not contributing covariates to the intestinal microbial community variance. Further, no bacterial phylotype was identified to significantly associate with these factors. However, breast milk feeding pattern and shorter duration infant antibiotic exposure were significantly associated with increased abundance of Clostridiales. More specifically, early full exclusive breast milk feeding by study day 10 (p-value=0.0001) and antibiotic exposure limited to no more than 4 days (p-value=0.05), were associated with the family Lachnospiraceae in the Clostridiales (p-value=0.004) (data not shown). On the other hand, Enterobacteriaceae, particularly *Klebsiella pneumoniae* (as identified by metagenomics sequencing), was significantly associated with full breast milk feeding achieved after study day 10 (p-value=0.01) (data not shown). These results strongly suggest members of the Clostridiales are significantly associated with low intestinal permeability, early full breast milk feeding, as well as shorter duration of antibiotic use.

F. Clostridiales Are Highly Prevalent in the GI Microbiota of Preterm Infants

The most abundant bacterial species that included *K. pneumoniae, Staphylococcus epidermidis, E. coli*, and *Enterococcus faecalis* were found with mean abundance of ~10-35% (S.D. ~ 15-30%) and ~85-95% prevalence in these samples. In comparison, many species such as *Streptococcus agalactiae, B. breve, B. longum, Clostridium perfringens, Propionibacterium acnes, Bacteroides fragilis, Veillonella parvula*, and *Streptococcus thermophiles* were present in 15-70% of all samples and had a much lower level of abundance ranging from ~0.0001-1% (S.D. ~ 0.0001-6%). Many of the members of Clostridiales were not resolved at the species or genus-level, while those taxonomically identified Clostridiales included *Coprococcus*, Blautia, SMB53, Ruminococcus gnavus, *Clostridium* spp., *Faecalibacterium prausnitzii*, Dorea, Ruminococcus bromii, *Roseburia*, Pseudoramibacter and Butyricicoccus pullicaecorum were detected in low or extremely low abundance yet high prevalence (data not shown). Given the average sequencing depth is ~$10^4$-$10^5$ and stool bacterial load per gram of stool is in the range of ~$10^6$-$10^{10}$ (Palmer et al., 2007; Abdulkadir et al., 2016; Wandro et al., 2018), it is likely that some bacterial taxonomic groups with low relative abundance (0.0001-1%) were below the detection limit. It is expected that the prevalence of the members of Clostridiales are underestimated and that is actually higher than the currently observed 15-70% among samples in the GI microbiota of preterm infants.

Preterm infants are at elevated risk for leaky gut, feeding intolerance, NEC and sepsis, and other short-term and long-term morbidities (Unger et al., 2015). The pathophysiology of these disorders is likely multifactorial, involving a combination of intestinal mucosa barrier immaturity, imbalance in microvascular tone, aberrant microbial colonization and altered immune responses (Mai et al., 2011; Neu and Walker, 2011; Unger et al., 2015). It has been previously demonstrated that neonatal factors such as gestational age, antibiotic exposure, and exclusive breastmilk feeding affect intestinal mucosa barrier permeability in preterm infants (Taylor et al., 2009; Saleem et al., 2017). With the rapid development of high-throughput sequencing technology, recent studies have evaluated the significant association between the composition of intestinal microbiota, neonatal intestinal health and development (Palmer et al., 2007; Neish, 2009; Belkaid and Hand, 2014; Warner et al., 2016). However, the relationships between intestinal microbiota and IP have not yet been evaluated in a high-risk preterm population. In this study, a particular focus was on the intestinal immaturity in the challenging, yet most demanding population of very early gestational age subjects, and the early development of the intestinal microbiota and its association with IP was investigated in preterm infants during the first 2 weeks of life. It was observed that neonatal factors known to be associated with low IP, including early exclusive breast milk feeding and shorter duration of antibiotic exposure, significantly associate with the early colonization of the intestinal microbiota by members of Clostridiales. Given that Clostridiales and *Bifidobacterium* are most transcriptionally active and are also the most abundant bacterial groups in later ages (6-18 months), suggesting a process in which colonization with these two bacterial groups early during intestinal development after birth appears critical.

The demonstrated association between IP, intestinal microbiota, and neonatal factors in this study suggest Clostridiales offer a new opportunity to develop a live biotherapeutic product (LBP) for the early prevention of NEC, possibly in combination with strains of *Lactobacillus* and *Bifidobacterium* already available. LBP therapies are promising, low-cost, and constitute a likely safe preventive measure to improve intestinal barrier maturation and reduce NEC incidence in at-risk preterm infants (Stratiki et al., 2007). There have been at least 11 randomized controlled trials and a recent meta-analysis of LBP supplementation to prevent NEC in preterm neonates (Deshpande et al., 2010; Bergmann et al., 2013). Although there was a 30% reduction in NEC incidence in these trials, various formulations, doses, and duration of therapy were used, infants<1000 g BW with the highest NEC incidence were under-represented, and no Food and Drug Administration-approved products are available to assure quality and safety under good manufacturing practices.

The taxonomic group Clostridiales was unfortunately known for a few pathogenic species that include C. botulinum, C. *perfringens*, C. *tetani*, and C. *difficile* in the family of Clostridiaceae (Rajilic-Stojanovic et al., 2007). However, Clostridiales has been largely overlooked because of the difficulties to culture in vitro. Recent application of culture-independent high-throughput sequencing identified many formerly unculturable Clostridiales species, and the group is now thought to be one of the predominant groups inhabiting the GI tract, comprising ~30-40% abundance of the adult intestinal microbiota and 13 bacterial families, and majority are commensal of the intestinal microbiota (Walker et al., 2011). In fact, Clostridiales are heterogeneous in terms of their enzymatic and metabolic properties with anti-inflammatory properties, which often associates with their fermentative metabolism of carbohydrates and amino acids that produces beneficial short-chain fatty acid (SCFA) such as acetate, propionate, and butyrate (Smith et al., 2013; Stefka et al., 2014). Further, Clostridiales have been recently shown to stimulate the production of intestinal epithelial cytokines that have been associated with the improvement of intestinal dysbiosis, and marked reduction in inflammation (Atarashi et al., 2011, 2013; Narushima et al., 2014). The recent characterization of 46 strains of newly isolated Clostridiales revealed their ability to induce regulatory T cells and a protection against colitis and allergic responses (Atarashi et al., 2011). Seventeen strains of human-derived Clostridiales species were rationally selected using gnotobiotic mice and the cocktail shown to have prophylactic effect in mouse colitis (Atarashi et al., 2013; Narushima et al., 2014). In addition, the administration of Clostridiales protects the host from pathogen infection and abrogated intestinal pathology (McMurtry et al., 2015). In term infants, the presence of Clostridiales in the intestinal microbiota was demonstrated to prevent colonization by bacterial pathogens such as S. *Typhimurium* (Kim et al., 2017). These species form the basis of the microbiome therapeutics product, SER109, for the treatment of ('. *difficile* infection in adults (Khanna et al., 2016). Future characterization of Clostridiales species will potentially prevent microbial community-mediated intestinal dysbiosis in preterm infants to optimize intestinal maturation and limit the burden of prematurity (Ward et al., 2016).

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

Abdulkadir, B., Nelson, A., Skeath, T., Marrs, E. C., Perry, J. D., Cummings, S. P., et al. (2016). Stool bacterial load in preterm infants with necrotizing enterocolitis. Early Hum. Dev. 95, 1-2.

Anand, R. J., Leaphart, C. L., Mollen, K. P., and Hackam, D. J. (2007). The role of the intestinal barrier in the pathogenesis of necrotizing enterocolitis. Shock 27,124-133.

Arrieta, M. C., Stiemsma, L. T., Amenyogbe, N., Brown, E. M., and Finlay, B. (2014). The intestinal microbiome in early life: health and disease. Front. Immunol. 5:427.

Arrieta, M. C., Stiemsma, L. T., Dimitriu, P. A., Thorson, L., Russell, S., Yurist-Doutsch, S., et al. (2015). Early infancy microbial and metabolic alterations affect risk of childhood asthma. Sci. Transl. Med. 7:307ra152.

Atarashi, K., Tanoue, T., Oshima, K., Suda, W., Nagano, Y., Nishikawa, H., et al. (2013). Treg induction by a rationally selected mixture of Clostridia strains from the human microbiota. Nature 500, 232-236.

Atarashi, K., Tanoue, T., Shima, T., Imaoka, A., Kuwahara, T., Momose, Y., et al. (2011). Induction of colonic regulatory T cells by indigenous *Clostridium* species. Science 331, 337-341.

Beach, R. C., Menzies, I. S., Clayden, G. S., and Scopes, J. W. (1982). Gastrointestinal permeability changes in the preterm neonate. Arch. Dis. Child. 57, 141-145.

Belkaid, Y., and Hand, T. W. (2014). Role of the microbiota in immunity and inflammation. Cell 157, 121-141.

Bergmann, K. R., Liu, S. X., Tian, R., Kushnir, A., Turner, J. R., Li, H. L., et al. (2013). Bifidobacteria stabilize claudins at tight junctions and prevent intestinal barrier dysfunction in mouse necrotizing enterocolitis. Am. J. Pathol. 182, 1595-1606.

Bolger, A. M., Lohse, M., and Usadel, B. (2014). Trimmomatic: a flexible trimmer for Illumina sequence data. Bioinformatics 30, 2114-2120.

Cenit, M. C., Olivares, M., Codoner-Franch, P., and Sanz, Y. (2015). Intestinal microbiota and celiac disease: cause, consequence or co-evolution? Nutrients 7, 6900-6923.

Cho, I., Yamanishi, S., Cox, L., Methe, B. A., Zavadil, J., Li, K., et al. (2012). Antibiotics in early life alter the murine colonic microbiome and adiposity. Nature 488, 621-626.

Church, D. M., Schneider, V. A., Graves, T., Auger, K., Cunningham, F., Bouk, N., et al. (2011). Modernizing reference genome assemblies. PLOS Biol. 9:e1001091.

de Muinck, E. J., and Trosvik, P. (2018). Individuality and convergence of the infant gut microbiota during the first year of life. Nat. Commun. 9:2233.

Deshpande, G., Rao, S., Patole, S., and Bulsara, M. (2010). Updated meta-analysis of probiotics for preventing necrotizing enterocolitis in preterm neonates. Pediatrics 125, 921-930.

Fadrosh, D. W., Ma, B., Gajer, P., Sengamalay, N., Ott, S., Brotman, R. M., et al. (2014). An improved dual-indexing approach for multiplexed 16S rRNA gene sequencing on the Illumina MiSeq platform. Microbiome 2:6.

Faulkner, J. R., and Minin, V. (2018). Locally adaptive smoothing with Markov random fields and shrinkage priors. Bayesian Anal. 13, 225-252.

Fisher, R. A. (1936). The use of multiple measurements in taxonomic problems. Ann. Eugenics 7, 179-188.

Fitzgibbons, S. C., Ching, Y., Yu, D., Carpenter, J., Kenny, M., Weldon, C., et al. (2009). Mortality of necrotizing enterocolitis expressed by birth weight categories. J. Pediatr. Surg. 44, 1072-1075; discussion 1075-1076.

Fox, T. P., and Godavitarne, C. (2012). What really causes necrotising enterocolitis? ISRN Gastroenterol. 2012: 628317.

Francisco, A. P., Bugalho, M., Ramirez, M., and Carrico, J. A. (2009). Global optimal eBURST analysis of multilocus typing data using a graphic matroid approach. BMC Bioinformatics 10:152.

Frank E, Hall M, Trigg L, Holmes G, Witten IH: Data mining in bioinformatics using Weka. Bioinformatics 2004, 20:2479-2481.

Franzosa, E. A., Hsu, T., Sirota-Madi, A., Shafquat, A., Abu-Ali, G., Morgan, X. C., et al. (2015). Sequencing and beyond: integrating molecular 'omics' for microbial community profiling. Nat. Rev. Microbiol. 13, 360-372.

Franzosa, E. A., Morgan, X. C., Segata, N., Waldron, L., Reyes, J., Earl, A. M., et al. (2014). Relating the metatranscriptome and metagenome of the human gut. Proc. Natl. Acad. Sci. U.S.A. 111, E2329-E2338.

Gevers, D., Kugathasan, S., Denson, L. A., Vazquez-Baeza, Y., Van Treuren, W., Ren, B., et al. (2014). The treatment-naive microbiome in new-onset Crohn's disease. Cell Host Microbe 15, 382-392.

Gorokhova, E. (2005). Effects of preservation and storage of microcrustaceans in RNAlater on RNA and DNA degradation. Limnol. Oceanogr. Methods 3, 143-148.

Grier, A., Qiu, X., Bandyopadhyay, S., Holden-Wiltse, J., Kessler, H. A., Gill, A. L., et al. (2017). Impact of prematurity and nutrition on the developing gut microbiome and preterm infant growth. Microbiome 5:158.

Guner, Y. S., Friedlich, P., Wee, C. P., Dorey, F., Camerini, V., and Upperman, J. S. (2009). State-based analysis of necrotizing enterocolitis outcomes. J. Surg. Res. 157, 21-29.

Haase A M et al. Dual sugar permeability testing in diarrheal disease. J Pediatr 2000; 136:232-7.

Hilsden R J et al. Intestinal permeability changes in response to acetylsalicylic acid in relatives of patients with Crohn's disease. Gastroenterology 1996; 110:1395-403.

Khanna, S., Pardi, D. S., Kelly, C. R., Kraft, C. S., Dhere, T., Henn, M. R., et al. (2016). A novel microbiome therapeutic increases gut microbial diversity and prevents recurrent clostridium Difficile infection. J. Infect. Dis. 214, 173-181.

Kim, Y. G., Sakamoto, K., Seo, S. U., Pickard, J. M., Gillilland, M. G. III, Pudlo, N. A., et al. (2017). Neonatal acquisition of Clostridia species protects against colonization by bacterial pathogens. Science 356, 315-319.

Koenig, J. E., Spor, A., Scalfone, N., Fricker, A. D., Stombaugh, J., Knight, R., et al. (2011). Succession of microbial consortia in the developing infant gut microbiome. Proc. Natl. Acad. Sci. U.S.A. 108(Suppl. 1), 4578-4585.

Langmead, B., Trapnell, C., Pop, M., and Salzberg, S. L. (2009). Ultrafast and memory-efficient alignment of short DNA sequences to the human genome. Genome Biol. 10:R25.

Liaw, A., and Wiener, M. (2002). Classification and regression by randomForest. R. News 2, 18-22.

Lin J et al. Expression of intestinal trefoil factor in developing rat intestine. Biol Neonate 1999; 76:92-97.

Mackie, R. I., Sghir, A., and Gaskins, H. R. (1999). Developmental microbial ecology of the neonatal gastrointestinal tract. Am. J. Clin. Nutr. 69, 1035S-1045S.

Madan, J. C., Farzan, S. F., Hibberd, P. L., and Karagas, M. R. (2012). Normal neonatal microbiome variation in relation to environmental factors, infection and allergy. Curr. Opin. Pediatr. 24, 753-759.

Maechler, M. (2016). cluster: "Finding Groups in Data": Cluster Analysis Extended Rousseeuw et al. Hoboken: JohnWiley & Sons, Inc.

Mai, V., Young, C. M., Ukhanova, M., Wang, X., Sun, Y., Casella, G., et al. (2011). Fecal microbiota in premature infants prior to necrotizing enterocolitis. PLOS One 6:e20647.

McMurtry, V. E., Gupta, R. W., Tran, L., Blanchard, E. E., Penn, D., Taylor, C. M., et al. (2015). Bacterial diversity and Clostridia abundance decrease with increasing severity of necrotizing enterocolitis. Microbiome 3:11.

Mishra A and Makharia GK. Techniques of functional and motility test: how to perform and interpret intestinal permeability. J Neurogastroenterol Motil 2012; 18:443-7.

Morton, J. T., Sanders, J., Quinn, R. A., McDonald, D., Gonzalez, A., Vazquez-Baeza, Y., et al. (2017). Balance trees reveal microbial niche differentiation. mSystems 2:e00162-16.

Mshvildadze, M., Neu, J., and Mai, V. (2008). Intestinal microbiota development in the premature neonate: establishment of a lasting commensal relationship? Nutr. Rev. 66, 658-663.

Narushima, S., Sugiura, Y., Oshima, K., Atarashi, K., Hattori, M., Suematsu, M., et al. (2014). Characterization of the 17 strains of regulatory T cell-inducing human-derived Clostridia. Gut Microbes 5, 333-339.

Nascimento, M., Sousa, A., Ramirez, M., Francisco, A. P., Carrico, J. A., and Vaz, C. (2017). PHYLOViZ 2.0: providing scalable data integration and visualization for multiple phylogenetic inference methods. Bioinformatics 33, 128-129.

Neish, A. S. (2009). Microbes in gastrointestinal health and disease. Gastroenterology 136, 65-80.

Neu, J., and Walker, W. A. (2011). Necrotizing enterocolitis. N. Engl. J. Med. 364, 255-264.

Oksanen, J., Blanchet, F. G., Kindt, R., Legendre, P., Minchin, P. R., O'Hara, R. B., et al. (2011). vegan: Community Ecology Package. R package version 2.0-2.

Palmer, C., Bik, E. M., Digiulio, D. B., Relman, D. A., and Brown, P. O. (2007). Development of the human infant intestinal microbiota. PLOS Biol. 5:e177.

Quast, C., Pruesse, E., Yilmaz, P., Gerken, J., Schweer, T., Yarza, P., et al. (2013). The SILVA ribosomal RNA gene database project: improved data processing and web-based tools. Nucleic Acids Res. 41, D590-D596.

Rajilic-Stojanovic, M., Smidt, H., and de Vos, W. M. (2007). Diversity of the human gastrointestinal tract microbiota revisited. Environ. Microbiol. 9, 2125-2136.

Ravel, J., Gajer, P., Abdo, Z., Schneider, G. M., Koenig, S. S., McCulle, S. L., et al. (2011). Vaginal microbiome of reproductive-age women. Proc. Natl. Acad. Sci. U.S.A. 108(Suppl. 1), 4680-4687.

Rotmistrovsky, K., and Agarwala, R. (2011). BMTagger: Best Match Tagger for Removing Human Reads from Metagenomics Datasets. Bethesda, MD: NCBI.

Rouwet, E. V., Heineman, E., Buurman, W. A., ter Riet, G., Ramsay, G., and Blanco, C. E. (2002). Intestinal permeability and carrier-mediated monosaccharide absorption in preterm neonates during the early postnatal period. Pediatr. Res. 51, 64-70.

Saleem, B., Okogbule-Wonodi, A. C., Fasano, A.,Magder, L. S., Ravel, J., Kapoor, S., et al. (2017). Intestinal barrier maturation in very low birthweight infants: relationship to feeding and antibiotic exposure. J. Pediatr. 183, 31.e1-36.e1.

Segata, N., Izard, J., Waldron, L., Gevers, D., Miropolsky, L., Garrett, W. S., et al. (2011). Metagenomic biomarker discovery and explanation. Genome Biol. 12:R60.

Segata, N., Waldron, L., Ballarini, A., Narasimhan, V., Jousson, O., and Huttenhower, C. (2012). Metagenomic microbial community profiling using unique clade-specific marker genes. Nat. Methods 9, 811-814.

Sellitto, M., Bai, G., Serena, G., Fricke, W. F., Sturgeon, C., Gajer, P., et al. (2012). Proof of concept of microbiome-metabolome analysis and delayed gluten exposure on celiac disease autoimmunity in genetically at-risk infants. PLOS One 7:e33387.

Sharon, I., Morowitz, M. J., Thomas, B. C., Costello, E. K., Relman, D. A., and Banfield, J. F. (2013). Time series community genomics analysis reveals rapid shifts in bacterial species, strains, and phage during infant gut colonization. Genome Res. 23, 111-120.

Smith, P. M., Howitt, M. R., Panikov, N., Michaud, M., Gallini, C. A., Bohlooly, Y. M., et al. (2013). The microbial metabolites, short-chain fatty acids, regulate colonic Treg cell homeostasis. Science 341, 569-573.

Stefka, A. T., Feehley, T., Tripathi, P., Qiu, J., McCoy, K., Mazmanian, S. K., et al. (2014). Commensal bacteria protect against food allergen sensitization. Proc. Natl. Acad. Sci. U.S.A. 111, 13145-13150.

Stratiki, Z., Costalos, C., Sevastiadou, S., Kastanidou, O., Skouroliakou, M., Giakoumatou, A., et al. (2007). The effect of a bifidobacter supplemented bovine milk on intestinal permeability of preterm infants. Early Hum. Dev. 83, 575-579.

Taylor, S. N., Basile, L. A., Ebeling, M., and Wagner, C. L. (2009). Intestinal permeability in preterm infants by feeding type: mother's milk versus formula. Breastfeed Med. 4, 11-15. Team, S. D. (2018). RStan: The R Interface to Stan. R Package Version 2.17.3.

Unger, S., Stintzi, A., Shah, P., Mack, D., and O'Connor, D. L. (2015). Gut microbiota of the very-low-birth-weight infant. Pediatr. Res. 77, 205-213.

Vatanen, T., Kostic, A. D., d'Hennezel, E., Siljander, H., Franzosa, E. A., Yassour, M., et al. (2016). Variation in microbiome LPS immunogenicity contributes to autoimmunity in humans. Cell 165, 842-853.

Walker, A. W., Ince, J., Duncan, S. H., Webster, L. M., Holtrop, G., Ze, X., et al. (2011). Dominant and diet-responsive groups of bacteria within the human colonic microbiota. ISME J. 5, 220-230.

Wandro, S., Osborne, S., Enriquez, C., Bixby, C., Arrieta, A., and Whiteson, K. (2018). The microbiome and metabolome of preterm infant stool are personalized and not driven by health outcomes, including necrotizing enterocolitis and late-onset sepsis. mSphere 3:e00104-18.

Ward, D. V., Scholz, M., Zolfo, M., Taft, D. H., Schibler, K. R., Tett, A., et al. (2016). Metagenomic sequencing with strain-level resolution implicates uropathogenic E. coli in necrotizing enterocolitis and mortality in preterm infants. Cell Rep. 14, 2912-2924.

Warner, B. B., Deych, E., Zhou, Y., Hall-Moore, C., Weinstock, G. M., Sodergren, E., et al. (2016). Gut bacteria dysbiosis and necrotising enterocolitis in very low birth-weight infants: a prospective case-control study. Lancet 387, 1928-1936.

Wei, T., and Simko, V. (2017). R package "corrplot": Visualization of a Correlation Matrix.

Yu, Y., Lu, L., Sun, J., Petrof, E. O., and Claud, E. C. (2016). Preterm infant gut microbiota affects intestinal epithelial development in a humanized microbiome gnotobiotic mouse model. Am. J. Physiol. Gastrointest. Liver Physiol. 311, G521-G532.

Zolfo, M., Tett, A., Jousson, O., Donati, C., and Segata, N. (2017). MetaMLST: multi-locus strain-level bacterial typing from metagenomic samples. Nucleic Acids Res. 45:e7.

What is claimed is:

1. A method of treating or preventing high intestinal permeability in a subject comprising:
   (a) determining the amount of Clostridiales and/or Bifidobacteriales bacteria in a sample obtained from a subject, and administering a therapeutically effective amount of a treatment or preventive agent for high intestinal permeability (IP) to the subject when the amount of Clostridiales and/or Bifidobacteriales bacteria in the sample is about 5% or less by relative abundance of the total amount of bacteria; or
   (b) determining the amount of Clostridiales and/or Bifidobacteriales bacteria in samples obtained from a subject at two or more time points and administering a therapeutically effective amount of a treatment or preventive agent for high intestinal permeability to the subject when the amount of Clostridiales and/or Bifidobacteriales bacteria in the samples decreases over time.

2. The method of claim 1, wherein the subject is a preterm infant.

3. The method of claim 2, wherein the preterm infant is an infant of less than 37 weeks of gestational age.

4. The method of claim 1, wherein the sample is a stool sample.

5. The method of claim 1, wherein a decrease in IP of at least 10% compared with a subject that does not receive the treatment or preventive agent for high intestinal permeability is achieved.

6. The method of claim 1, wherein the amount of bacteria in the sample is based on the relative abundance of one or more selected genes corresponding to the bacteria in the sample.

7. The method of claim 1, wherein the amount of bacteria in the sample is based on the relative abundance of a 16S rRNA gene variable region of the bacteria in the sample.

8. The method of claim 1, wherein the amount of bacteria in the sample is based on the relative abundance of the V3-V4 variable region of a 16S rRNA gene of the bacteria in the sample.

9. The method of claim 1, wherein when samples are obtained from a subject at two or more time points in (be), the time points are separated by at least 7 days plus or minus 1 to 2 days.

10. The method of claim 1, wherein the decrease in the amount of Clostridiales and/or Bifidobacteriales bacteria in the samples in over time in (be) is a decrease of at least about 10%.

11. The method of claim 1, wherein the treatment is one or more of live biotherapeutic product (LBP), antibiotics, prebiotics, synbiotics, and intestinal environment parameters modifying small molecules.

12. The method of claim 1, wherein the preventive agent is one or more of LBP, antibiotics, prebiotics, synbiotics, and intestinal environment parameters modifying small molecules.

13. The method of claim 1, further comprising administering breast milk to the subject or reducing exposure of the subject to antibiotics, or both.

14. A method of treating or preventing high intestinal permeability in a subject comprising:
   (a) determining the amount of Clostridiales bacteria in a sample obtained from a subject, and administering a therapeutically effective amount of a treatment or preventive agent for high intestinal permeability (IP) to the subject when the amount of Clostridiales and/or Bifidobacteriales bacteria in the sample is about 5% or less by relative abundance of the total amount of bacteria;
   (b) determining the amount of Clostridiales bacteria in a sample obtained from a subject, and administering a therapeutically effective amount of a treatment or preventive agent for high intestinal permeability to the subject when the amount of Clostridiales and/or Bifidobacteriales bacteria is within a pre-established range of amounts of Clostridiales and/or Bifidobacteriales bacteria associated with high intestinal permeability; or (c) determining the amount of Clostridiales bacteria in samples obtained from a subject at two or more time points and administering a therapeutically effective amount of a treatment or preventive agent for high intestinal permeability to the subject when the amount of Clostridiales and/or Bifidobacteriales bacteria in the samples decreases over time.

15. The method of claim 14, wherein the subject is a preterm infant.

16. The method of claim 15, wherein the preterm infant is an infant of less than 37 weeks of gestational age.

17. The method of claim 14, wherein the sample is a stool sample.

18. The method of claim 14, wherein a decrease in IP of at least 10% compared with a subject that does not receive the treatment or preventive agent for high intestinal permeability is achieved.

19. The method of claim 14, wherein the amount of bacteria in the sample is based on the relative abundance of one or more selected genes corresponding to the bacteria in the sample.

20. The method of claim 14, wherein the amount of bacteria in the sample is based on the relative abundance of a 16S rRNA gene variable region of the bacteria in the sample.

21. The method of claim 14, wherein the amount of bacteria in the sample is based on the relative abundance of the V3-V4 variable region of a 16S rRNA gene of the bacteria in the sample.

22. The method of claim 14, wherein when samples are obtained from a subject at two or more time points in (c), the time points are separated by at least 7 days plus or minus 1 to 2 days.

23. The method of claim 14, wherein the decrease in the amount of Clostridiales bacteria in the samples in over time in (c) is a decrease of at least about 10%.

24. The method of claim 14, wherein the treatment is one or more of live biotherapeutic product (LBP), antibiotics, prebiotics, synbiotics, and intestinal environment parameters modifying small molecules.

25. The method of claim 14, wherein the preventive agent is one or more of LBP, antibiotics, prebiotics, synbiotics, and intestinal environment parameters modifying small molecules.

26. The method of claim 14, further comprising administering breast milk to the subject or reducing exposure of the subject to antibiotics, or both.

* * * * *